Figure 2:
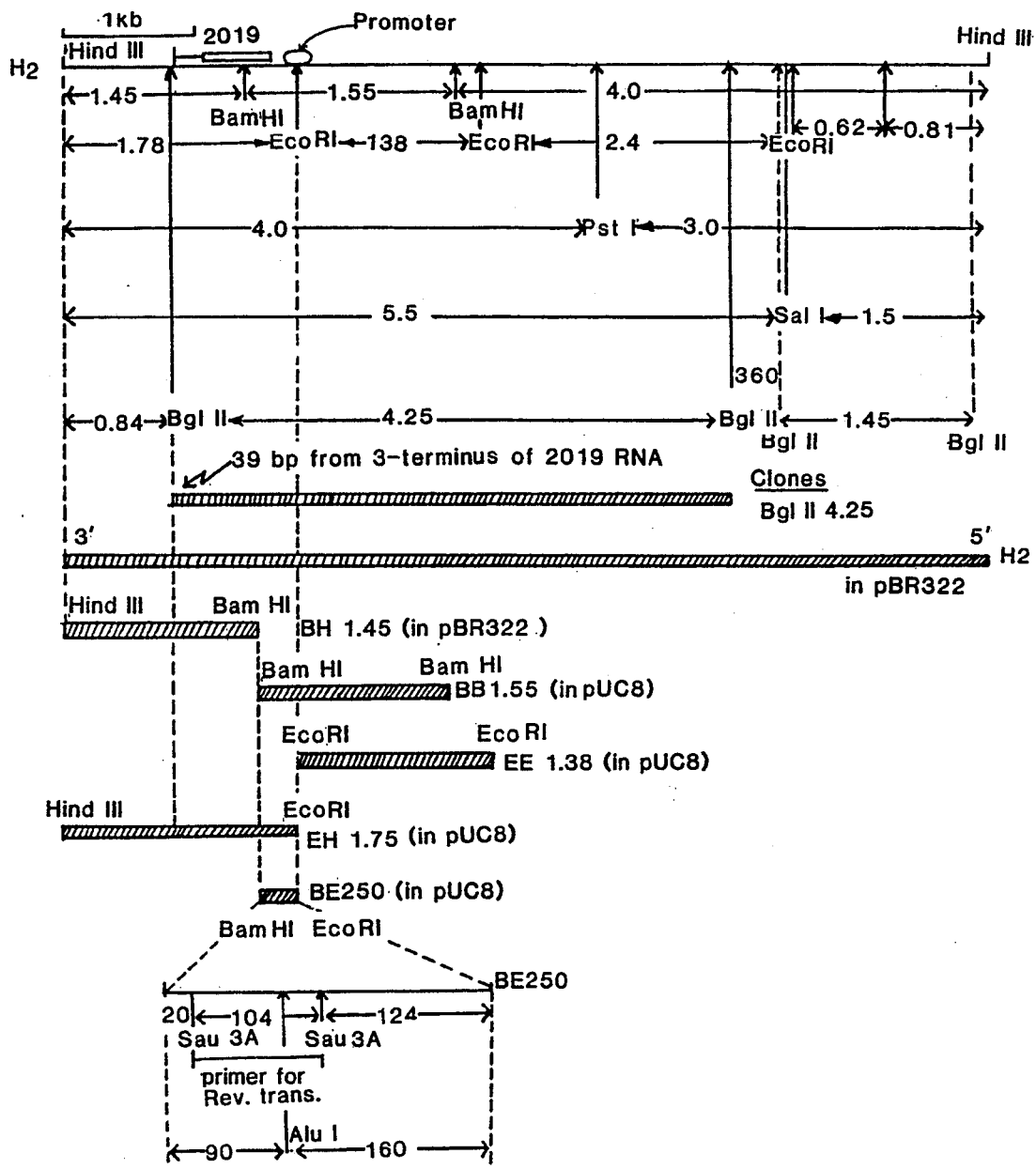

United States Patent [19]

Key et al.

[11] Patent Number: 5,447,858
[45] Date of Patent: Sep. 5, 1995

[54] HEAT SHOCK PROMOTER AND GENE

[75] Inventors: Joe L. Key, Boulder, Colo.; William B. Gurley, Gainesville, Fla.; Ronald T. Nagao, Athens, Ga.; Friedrich Schoeffl, Bielefeld, Germany; Eva Czarnecka, Gainesville, Fla.

[73] Assignee: Mycogen Plant Sciences, Inc., San Diego, Calif.

[21] Appl. No.: 599,993

[22] Filed: Apr. 13, 1984

[51] Int. Cl.$^6$ .................. C12N 5/14; C12N 15/29; C12N 15/82; C12N 15/32
[52] U.S. Cl. .................. 435/172.3; 435/69.1; 435/70.1; 435/252.2; 435/252.3; 435/252.33; 435/320.1; 536/24.1
[58] Field of Search .................. 435/172.3, 240, 68, 435/317, 253, 320, 69.1, 70.1, 252.2, 252.3, 252.33, 320.1; 935/6, 24, 30, 35, 41, 43, 56, 64, 67; 536/27, 24.1; 800/1

[56] References Cited

U.S. PATENT DOCUMENTS 4,459,355  7/1984  Cello et al. .................. 435/172.3

OTHER PUBLICATIONS

Kaluza et al. 1985. FEBS Lett. 188(1):37–42.
Ohgawara et al. 1983. Protoplasma 116: 145–148.
Otten et al. 1981, Mol. Gen. Genet. 183: 209–213.
DeGeve et al. 1982. Nature 300: 752–755.
Fraley et al. (1983) "Expression of bacterial genes . . ." PNAS USA 80: 4803–4807.
Hoekema et al. 1984 "Delivery of T-DNA from the *Agrobacterium tumefaciens* chromosome into plant cells" *EMBO J.* vol. 3 2485–90.
Schnepf et al. 1981 "Cloning and Expression of the *Bacillus thuringiensis* crystal protein gene . . ." *Proc Natl Acad* vol. 78 2893–2897.
Hooykaas et al. 1984 "The Molecular Genetics of Crown Gall Tumorigenesis" in *Adv. in Gen* vol. 22 pp. 209, 225–246.
Comai et al. 1983 "An altered aro A Product Confers Resistance to the Herbicide Glyphosate" *Science* vol. 221 370–371.

R. W. Olds et al. (1980) Principles of Gene Manipulation, p. 20.
Hernalsteens et al. (1984) EMBO J. 3:3039–3041.
Hooykaas-Van Slogteren et al. (1984) Nature 311:763–764.
Nomenclature Committee of the International Union of Biochemistry (1986) J. Bio. Chem. 261:13–17.
Herrera-Estrella et al. (1983) Nature 303:209–213.
Edens et al. (1982) Gene 18:1–12.
Gurley et al. (1986) Mol. & Cell. Biol. 6:559–565.
Marx, J. L. (1985) Science 230:1148–1150.
Herrera-Estrella et al. (1985) in *Plant Genetic Engineering,* J. H. Dodds (ed.) Cambridge Univeristy Press, Cambridge, UK, pp. 61–93.
Ohta, Y. (1986) Proc. Natl. Acad. Sci. USA 83:715–719.
Hain et al. (1985) Mol. Gen. Genet. 199:161–168.
Potrykus et al. (1985) Mol. Gen. Genet. 199:183–188.
Potrykus et al. (1985) 199:169–177.
Fromm et al. (1985) Proc. Natl. Acad. Sci. USA 82:5824–5828.
Spena et al. (1985) EMBO J. 4:2739–2743.
Barnett, T. et al. (1980) Dev. Genet. 1:331–340.
Palham. H. R. B. and M. Biez (1982) EMBO J. 1:1473–1477.
Holmgren, R. et al. (1981) Proc. Nat. Acad. Sci. USA 78:3775–3778.

(List continued on next page.)

*Primary Examiner*—David T. Fox
*Attorney, Agent, or Firm*—Saliwanchik & Saliwanchik

[57] ABSTRACT

A plant heat shock promoter has been isolated from soybean, sequenced and shown to induce gene expression in response to a temporary heat shock. This invention utilizes the disclosed plant heat shock promoters for the construction of promoter/structural gene chimeras which are expressible in plant cells in response to heat shock. The reporter gene β-galactosidase was expressed transiently in response to a heat shock signal. Further, this invention permits application of heat shock inducible chimeras as a detection method for successful transformation of plant cells.

42 Claims, 13 Drawing Sheets

OTHER PUBLICATIONS

Pelham, H. R. B. (1982) Cell 30:517–528.

Li, G. C. and G. M. Hahn (1978) Nature 274:699–701.

Henle, K. J. and L. A. Dethlefsen (1978) Cancer Res. 38:1843–1851.

Mitchell, H. K. et al. (1979) Dev. Genet. 1:181–192.

McAlister, L. and D. B. Finkelstein (1980) Biochem. Biophys. Res. Comms. 93:819–824.

Key, J. L. et al. (1981) Proc. Nat. Acad. Sci. USA 78:3526–3530.

Storti, R. V. et al. (1980) Cell 22:825–834.

Dawson, W. O. and G. L. Grantham (1981) Biochem. Biophys. Res. Commun. 100:23–30.

Schoffl, F. and J. L. Key (1982) J. Mol. Appl. Genet. 1:301–314.

Key, J. L. et al. (1982) In: Heat Shock from Bacteria to Man (Schlestinger, M. J.; Ashburner, M. And A. Tissieres, eds.) Cold Spring Harbor Laboratory, pp. 329–336.

Key, J. L. et al. (1983) In; Current Topics In Plant Biochemistry and Physiology (Randall, D. D., Blevins, D. G., Larson, R. L. and B. J. Rapp, eds.) vol. 2 Univ. of Missouri, Columiba pp. 107–117.

Schlesinger, M. et al. (1982) In: Heat Shock from Bacteria to Man (Schlestinger, M. J., Ashburner, M. and A. Tissieres, eds.) Cold Springs Harbor Laboratory, pp. 243–250.

Key. J. L. et al. (1983) In: NATO Advanced Studies Workshop on Genome Organization and Expression in Plants (L. Dure, ed.) Plenum Press.

Schlesinger, M. J. et al. (1982) Trends Biochem. Sci. 1:222–225.

Hacket, R. W. and J. T. Lis (1983) Nucleic Acids Res. 11L7011–7030.

Ingolia, T. D. and E. A. Craig (1982) Proc. Nat. Acad. Sci. USA 79:2360–2364.

Southgate, R. et al. (1983) J. Mol. Biol. 165:35–67.

Schoffl, F. and J. L. Key (1983) Plant. Mol. Biol. 2:269–278.

FIG. IA

```
         130       140       150       160       170       180
          *         *         *         *         *         *
    ATGATGATGAAAAATGGAAAAACCTACTAATGTATTTATGAATAATGTCCAGAAGTGGAA 190       200       210       220       230       240
          *         *         *         *         *         *
    GAAAAATAAATATAATGATGTGTAGTAAACAAGAACCTTCGTACATGGTGTGGAGAATTT
         MboI                              RsaI        EcoRI
                                                       EcoRI'
                                                       EcoRI*

"CAT" box            concensus
         250       260       270       280       290       300
          *         *         *         *         *         *
    AACCAAATTGCAAAAAGTAGGATTTTTCTGGAACATACAAGATTATCCTTTCACTTCCTT
        EcoRI*        EcoRI'

"TATA" box
         310       320       330       340       350       360
          *         *         *         *         *         *
    TAAATACCTCGCGTATCCCCTTCGTCCTCGTCAAACGAAGAAAAAAGTTACCTGTTTGCG
    AhaIII    ThaI   MnlI     ↑      MnlI         MboII     MboI
                        +1 transcription                    Sau3A 370       380       390       400       410       420
          *         *         *         *         * start   *
    ATCTCATTACAATCTCCCTAGTTTCTAATCTCAGCTAAGAAAAACCAAAAGATGTCTCTG
                             DdeIAluI                       HinfI
                             DdeI 430       440       450       460       470       480
          *         *         *         *         *         *
    ATTCCAGGTTTCTTCGGTGGCCGAAGGAGCAACGTCTTCGATCCATTCTCACTCGACATG
        BstNI     HaeIII MboI          MboI          TaqI
        EcoRII                         Sau3A
        MboII                          TaqI
        ScrFI 490       500       510       520       530       540
          *         *         *         *         *         *
    TGGGATCCCTTCAAGGATTTTCATGTTCCCACTTCTTCTGTTTCTGCTGAAAATTCTGCA
       BamHI      EcoRI' MboII                          EcoRI'
       EcoRI'                                           EcoRI*
       MboI
       Sau3A
```

FIG. 1B

```
      550        560        570        580        590        600
       *          *          *          *          *          *
TTCGTGAGCACTCGTGTGGATTGGAAGGAGACCCCAGAGGCACACGTGTTCAAGGCTGAT
        HgiAI               MnlI 610        620        630        640        650        660
       *          *          *          *          *          *
ATTCAAGGGCTGAAGAAAGAGGAAGTCAAGGTTCAGATTGAAGATGATAGGGTTCTTCAG
      MnlI           MboII               MboII MboII 670        680        690        700        710        720
       *          *          *          *          *          *
ATTAGCGGAGAGAGGAACGTTGAAAAGGAAGACAAGAACGACACGTGGCATCGCGTGGAG
 MnlI                                       MboII      ThaISfaNI 730        740        750        760        770        780
       *          *          *          *          *          *
CGTAGCAGTGGTAAGTTCACGAGAAGGTTCAGATTGCCGGAGAATGCAAAAGTGAATGAA
                                    HpaII 790        800        810        820        830        840
       *          *          *          *          *          *
GTGAAGGCTTCTATGGAAAATGGGGTTCTCACTGTCACTGTTCCTAAGGAAGAGGTTAAG
                                              DdeI
                                              MnlI
                                              MstII 850        860        870        880        890        900
       *          *          *  stop   *          *          *
AAGCCTGATGTTAAGGCCATTGAAATCTCTGGTTGATCCATGTTATGGTTGAAAATCGTG
MboII          HaeIII   EcoRI'  MboI
                                Sau3A 910        920        930        940        950        960
       *          *          *          *          *          *
AGCTTATCCTTTGTTGTTGTAATAAGTGTCTTCTGTCTTGTGTGCCTTTGAGAAAAATCT
 AluI                 MboII                         MboII EcoRI'

970
       *
TCCATGCATGCATTGT
     SphI
```

FIG. 3

```
pM2005                           A A T A T T T T G A A T A A C A C A T T T T T
pL2005                           G A A T T C T G A A A T T G G G T C T T T T T
hs6871  T T A T T A A A A A T A C A A A T T T A T A A A T T A A G T T C A A C T C A pM2005  T T T T T A A T A T T C T G A A A A A T A T T T T T C A G A A C A C A A C A
pL2005  T T G T G G G C A C T T T T T G A T G T - T T T T G T T T A A G T T A C T G
hs6871  T C C T A T C T C A C T C T T T A A A T A C G A T G T T T A C T T A T T A G pM2005  A T A T T T C A G A A T T T A T A G G T A - C A A A G A T T T T A A T A A A
pL2005  T A C T G T G G G C C A C A A A A C G T A T A G A T C A A A G T A G T A A T
hs6871  A C T C A T T A A T A A A A A A A A A A A A A T C A T T T G T A C A A A G pE2019                    5'- A T G A T G A T G A A A A A T G G A A A A A C
pM2005  A A A G G A T G G T G A A T A T A G C A A A A G C C T A T T T A T G A A C G
pL2005  A A - - - T A A T A T T G A T T A A A T G A T A T A T A T A T A T A T A T A
hs6871  C C C A C C A T A A A G G C A A T T T G G G C C T G G T A G A C C A A T C C pE2019  C T A C T A A T G T A T T T A T G A A T A A T G T C C A G A A G T G G A - -
pM2005  A T A T C A A C C A G A A C T A G A A C A A G A A A A A T A A A T G C A C T
pL2005  T A T A T A T A T A T A T C T A G - A A G G T T G T A G A A G A C T A G C T
hs6871  T A A C C A A T G T C T G G T T A A G A T G G T C C A A T C C C G A A A C T pE2019  A G A A A A A T A A A T A T A A T - G A G G T G T A G T A A A C A A G A - -
pM2005  A G A A C C T T C G T A C A C G G A G T G G G A G A A G T C C A G A A G T T T
pL2005  A G A A C G T A C G T A - T T C G T G T G G A G A A G T C C T G A A G T - -
hs6871  T C T A G T T G C G G T T C G A A G A A G C C A G A A T G T T T C T G A A A pE2019  A C C T T C G T A C A T - - - - - G G T G T G G A G A A T T C A A C C A A
pM2005  T T A T A G A A T C A T T T G A A A C T G - - - - - - G T A A A A C C A A
pL2005  T T A T C G A A T C A T C T - A A A A C T G C T A A A A T A G C A A A - C A A
hs6871  G T T T C A G A A A A T T C T A G T T T T G A G A T T T T C A G A A G T A C pE2019  - - - - - - A T T G C A A A A G T A G G A T T T T T C T G G A A C A T A
pM2005  C C A A - - A T T G C - - A A A - C A C G A T T T T T C T G G A A C G T A
pL2005  C A T T A T A T T G T - - A A A - C A A T A T T T T T C T G G A A C A T A
hs6871  G G C A T G A T G A T G C A T A A C A A G G A C T T T T C T C G A A A G T A
                                                        consensus sequence pE2019  C A A G A T T A - T C C T T T C A C T T C C T T T A A A T A C - - - - C T C G
pM2005  C A C T A T T A - T C C T T T C A C T T A C T T T A A A T A C - - A T C A C G
pL2005  C A A G A G T A - T C C T T T C A C T T C C T T T A A A T A C C T C G A G T G
hs6871  C T A T A T T G C T C C T C T A C A T G A T T T T A A A T A C C C C A T G T pE2019  C G T A T C C C C T T C G T C C T C G T C A A A C G A A G A - - - A - A A A
pM2005  A T T A G T C A G A A A A A C G A A A C G A A G A A A A G A G T T A C A - A
pL2005  - T C C C C A T T G A C T C A T C A A A C A A G A G A A G A G T T A C A G A
hs6871  C C T T T G A A G A C A C A T C A C A G A A A G A A G T G A A G G C A T C G pE2019  A G T T A C C T G T T T G C G A T C T C A T T A C A A T C T C C C T A G T T
pM2005  A G T T A C C T G T A T A C G A T C T C A T T T T G A T C T C C C A A G T T
pL2005  A - T T C C T G T T T A C G A T C T C A T T A C A A T T T T G C A A C T T
hs6871  T T A G C A G T T T T G T A G A T T C A A C C T C A A T T T G C A G A G T T pE2019  T C T A A - - - T C T C A G C T A A G A A A - - A - - A C C A A A A G A T G
pM2005  T C A A A - - - T C T C - G C G A A T A A A - T A T - A T C A A A A G A T G
pL2005  T C A A A G C T T A T T A G C - - - T A A A G T A A C A T C A A A A G A T G
hs6871  A C G T T C T A A T A T A T T T A C A C A A G A C T G A T A A G A G A A A A T G
```

FIG. 4A

| | | | | | | | | | | | | |
|---|---|---|---|---|---|---|---|---|---|---|---|---|
| pE2019 | \|A T G\| | T C T\| | C T G\| | A T T\| | C C A\| | G G T\| | T T C\| | T T C\| | G G T\| | G G C\| | C G A\| | A G G\| |
| | Met | Ser | Leu | Ile | Pro | Gly | Phe | Phe | Gly | Gly | Arg | Arg |
| pM2005 | \| | \| | \| | \| | \| | \|A | \|A T\| | \| | \| | \|A | \| | \| |
| | | | | | | Ser | Ile | | | | | |
| pL2005 | \| | \| A\|T | \| | \| | \|A | \|A T\| | \| | \| | \| C \| | \| | | |
| | | | | | Ser | Ile | | | | Pro | | |
| hs6871 | \| | \| | \| | \| | \| | \|A | \| | \| | \| | \| | \| | \| |
| | | | | | | Ser | | | | | | |

| | | | | | | | | | | | | |
|---|---|---|---|---|---|---|---|---|---|---|---|---|
| pE2019 | \|A G C\| | A A C\| | G T C\| | T T C\| | G A T\| | C C A\| | T T C\| | T C A\| | C T C\| | G A C\| | A T G\| | T G G\| |
| | Ser | Asn | Val | Phe | Asp | Pro | Phe | Ser | Leu | Asp | Met | Trp |
| pM2005 | \| | \| | \| G\| | \| | \| | \| T\| | \| | \| C\| | \| | \|G | \| | \| |
| | | | | | | | | | | Val | | |
| pL2005 | \| | \| | \| G\| | \| | \| | \| | \| | \| | \| | \| T\| | \| | \| |
| hs6871 | \| | \| G T\| | T\| | \| | C\| | T\| | \| | C\| | \| | T\|G | \| | \| |
| | | Ser | | | | | | | | Val | | |

BamHI

| | | | | | | | | | | | | |
|---|---|---|---|---|---|---|---|---|---|---|---|---|
| pE2019 | \|G A T\| | C C C\| | T T C\| | A A G\| | G A T\| | T T T\| | C A T\| | G T T\| | C C C\| | A C T\| | T C T\| | T C T\| |
| | Asp | Pro | Phe | Lys | Asp | Phe | His | Val | Pro | Thr | Ser | Ser |
| pM2005 | \| | \| | \| | \| | \| | \| | \| | \|T | \| | \| | \| | \|C T \| |
| | | | | | | | | Phe | | | | Leu |
| pL2005 | \| | \| | \| | \| | \| | \| | \| | \| A | \| | \| | \| | \| |
| | | | | | | | | Tyr | | | | |
| hs6871 | \| | C\| | \| | \| | \| | \| | \| | \| | \| | \| G \| | \|C T \| | |
| | | | | | | | | *Del | | Ser | Leu | |

| | | | | | | | | | | | | |
|---|---|---|---|---|---|---|---|---|---|---|---|---|
| pE2019 | \|G T T\| | T C T\| | G C T\| | G A A\| | A A T\| | T C T\| | G C A\| | T T C\| | G T G\| | A G C\| | A C T\| | C G T\| |
| | Val | Ser | Ala | Glu | Asn | Ser | Ala | Phe | Val | Ser | Thr | Arg |
| pM2005 | \|*Del \| | \| | \| | \| | \| | \| | \| | T\| | \| A \| | \| | \| | |
| | | | | | | | | | Asn | | | |
| pL2005 | \| | \| | \| | \| | \| | \| | \| | T\| | \| A \| | .A\| | \| | |
| | | | | | | | | | Asn | | | |
| hs6871 | \|*Del \| | \| | \| | \| | A\| | G\| | T\| | \| | \| | A\| | A\| | |

| | | | | | | | | | | | | |
|---|---|---|---|---|---|---|---|---|---|---|---|---|
| pE2019 | \|G T G\| | G A T\| | T G G\| | A A G\| | G A G\| | A C C\| | C C A\| | G A G\| | G C A\| | C A C\| | G T G\| | T T C\| |
| | Val | Asp | Trp | Lys | Glu | Thr | Pro | Glu | Ala | His | Val | Phe |
| pM2005 | \| | \| | \| | \| A\| | A\| | \| | \| A\| | \| | \| | \| | \| | |
| pL2005 | \| | \| | \| | \| | \| | \| A \| | \| | \| | \| | \|C | \| | |
| | | | | | | Gln | | | | Leu | | |
| hs6871 | \| | \| | \| | \| A\| | \| | A\| | \| | \| | \| | \| | \| | |

FIG. 4B

```
pE2019  |A A G|G C T|G A T|A T T|C C A|G G G|C T G|A A G|A A A|G A G|G A A|G T C|
         Lys   Ala   Asp   Ile   Pro   Gly   Leu   Lys   Lys   Glu   Glu   Val
pM2005  |G    |     |     |     |     |     |     |     |    G|     |     |    G|
         Glu
pL2005  |     |     |     |     |     |     |     |     |     |     |     |    G| hs6871  |     |     |     |     |     |     |     |     |    G|     |     |    G| pE2019  |A A G|T T C|A G A|T T G|A A G|A T G|A T A|G G T|T C T|T C A|G A T|
         Lys   Val   Gln   Ile   Glu   Asp   Asp   Arg   Val   Leu   Gln   Ile
pM2005  |     |     |     |     |     |     |     |     |     |     |     |   A| pL2005  |     |     |     |     |     |     |     |     |     |     |     |    | hs6871  |     |C   G|G    |     |C    |     | G C |    A|     |     |     |   A|
              Leu   Glu         Gln          Gly pE2019  |A G C|G G A|G A G|A G G|A A C|G T T|G A A|A A G|G A A|G A C|A A G|A A C|
         Ser   Gly   Glu   Arg   Asn   Val   Glu   Lys   Glu   Asp   Lys   Asn
pM2005  |     |     |     |     |     |C    |    G|     |     |     |     |     |
                                       Leu
pL2005  |     |     |     |     |     |     |    G|     |     |     |     |     | hs6871  |     |     |     |     |     |    T|     |     |    A|     |     |    T| pE2019  |G A C|A C G|T G G|C A T|C G C|G T G|G A G|C G T|A G C|A G T|G G T|A A G|
         Asp   Thr   Trp   His   Arg   Val   Glu   Arg   Ser   Ser   Gly   Lys
pM2005  |     |     |     |     |     |     |     |     |    C|    C|     |    C|
                                                                              Asn
pL2005  |     |     |     |     |     |     |    C|     |     |    A|     |     |
                                             Asp
hs6871  |    T|     |     |     |     |     |     |    T|     |    C|     |     | pE2019  |T T C|A C G|A G A|A G G|T T C|A G A|T T G|C C G|G A G|A A T|G C A|A A A|
         Phe   Thr   Arg   Arg   Phe   Arg   Leu   Pro   Glu   Asn   Ala   Lys
pM2005  |     |   T |    G|     |     |    G|     |     |     |    T|     |     |
               Met
pL2005  |     |   T |     |     |     |     |     |    A|     |     |     |     |
               Met
hs6871  |    G|G T  |    G|     |   T |     |     |     |     |    T|     |     |
         Leu  Val
```

FIG. 4C

```
pE2019  |G T G|A A T|G A A|G T G|A A G|C T|T.C T|A T G|A A A|A T|G G G|G T T|
         Val   Asn   Glu   Val   Lys   Ala   Ser   Met   Glu   Asn   Gly   Val
pM2005  |     |G   G|C    |     |     |     |     |     |     |     |     T|     |
              Glu   Gln
pL2005  |     |C  A| T    |*Del |     |  G  |     |     |     |     |     |     |
              Gln   Val                  Cys
hs6871  |     |G  C|C    |     |     |     |  C| |     |     |     |     |     |
              Asp   Gln pE2019  |C T C|A C T|G T C|A C T|G T T|C C T|A A G|G A A|G A G|G T T|A A G|A A G|
         Leu   Thr   Val   Thr   Val   Pro   Lys   Glu   Glu   Val   Lys   Lys
pM2005  |     |   A|    T|C T C|A C A|G T T|T A C|C G.T|G C C|C A A|A G A|A G A|
                          Leu   Thr   Val   Tyr   Arg   Ser   Gln   Arg   Arg
pL2005  |     |     |    T|    |A   |   A| |     |     |     |     |A|G A A|
                                Ile                                         Glu
hs6871  |     |     |    A|    |     |     |     |     |     |A   |     |     |
                                                                      Ile pE2019  |C C T|G A T|G T T|A A G|G C C|A T T|G A A|A T C|T C T|G G T|T G A|T C C|
         Pro   Asp   Val   Lys   Ala   Ile   Glu   Ile   Ser   Gly   stop
pM2005  |G G T|T A A|G A A|
         Gly   stop
pL2005  |A G T|C T G|A T G|T T A|A G C|C T A|T A A|G A A|
         Ser   Leu   Met   Leu   Ser   Leu   stop
hs6871  |     |     |     |     |     |     |A|   C|    |     |     |A|   |     |
                                          Asp
```

Note: Blank spaces indicate identity with the nucleotide sequence or the amino acid sequence.

*Del – indicates a deletion of a codon(s).

```
         4         14        24        34        44        54        64        74        84
5'       TCAGAAAAAAATTCATTATATTGATATAAATATTCATTAATTTATCAATAATTTATATTGAGAAATCTAGATAGTC
  94 _  AGCCTTTAAGAGATAGAATTTAAAATATAATTGGGTAAAACATTATTAAAAATACAAATTTATAAAATTAAGTTCAACTCATCTATCTCACTCTTTAA
                  104       114       124       134       144       154       164       174       184
-500
 194 _  ATACGATGTTACTTATTAGACTCATTAATAAAAAAAAAAAAATCATTTGTACAAAGCCCACCATAAAGGCAATTTGGGCCTAGGACCAATCCTAAC
                  204       214       224       234       244       254       264       274       284
-400
 294 _  CAATGTCTGGTTAAGATGGTCCAATCCCGAAACTTCTAGTTGCGGTTGCGAAGAAGCCAGAATGTTTCTGAAAGTTTCAGAAAATTCTAGTTTTGAGATTT
                  304       314       324       334       344       354       364       374       384
-300
 394 _  TCAGAAGTACGGCATGATGATGCATAACAAGGACTTTCTCGAAAGTACTATATTGCTCCTCTACATCATTTAAATACCCATGTGTCCTTTGAAGACAC
                  404       414       424       434       444       454       464       474       484
-200
 494 _  ATCACAGAAAGAAGTGAAGGCATCGTTAGCAGTTTTGTAGATTCAACCTCAATTTGCAGAGTTACGTTCTAATATATTTACACAAGAGACTGATAAGAGAAA
                  504       514       524       534       544       554       564       574       584
-100
        Met Ser Leu Ile Pro Ser Phe Phe Gly Arg Arg Ser Arg Ser Leu Asp Pro Phe Ser Leu Asp Val Trp Asp   +75
        ATG TCT CTG ATT CCA AGT TTC TTC GGT GGC CGA AGG AGC AGT GTT TTC GAC CCT TTC TCC CTC GAT GTG TGG GAC

Pro Phe Lys Asp Phe Pro Phe Pro Ser Ser Leu Val Phe Pro Val Ala Phe Val Ser Thr Arg Val Asp Trp   +150
        CCC TTC AAG GAT TTT CCA TTT CCC AGT TCT CTT GTT TTC CCC GTT GCT TTT GTG AGC ACA CGA GTG GAT TGG

Lys Glu Thr Pro Glu Ala His Val Phe Lys Ala Asp Ile Pro Gly Leu Lys Lys Glu Val Lys Leu Glu Ile   +225
        AAG GAG ACA CCA GAA GCA CAC GTG TTC AAG GCT GAT ATT CCA GGG CTG AAG AAG GAG GTG AAG CTG GAG ATT

Gln Asp Gly Arg Val Leu Gln Ile Ser Gly Glu Glu Asn Val Glu Lys Asp Asn Asp Thr Trp His Arg     +300
        CAA GAT GGC AGA GTT CTT CAG ATA AGC GGA GAG GAG AAT GTT GAA AAA GAA GAC AAT GAT ACG TGG CAT CGC

Val Glu Arg Ser Ser Gly Lys Leu Val Arg Arg Phe Leu Pro Glu Asn Ala Lys Val Asp Gln Val Lys Ala +375
        GTG GAG CGA AGC AGT GGC AAG TTG GTG AGG AGG TTT AGA TTG CCG GAG AAT GCT AAA GTG GAC CAA GTG AAG GCT

Ser Met Glu Asn Gly Val Leu Thr Thr Val Pro Lys Glu Ile Lys Lys Pro Asp Val Lys Ala Ile Asp     +450
        TCC ATG GAA AAT GGG GTT CTC ACT GTA ACT GTT CCT AAG GAG ATT AAG AAG CCT GAT GTT AAG GCC ATA GAC
```

FIG. 9B

```
Ile Ser Gly OCHRE
ATC TCT GGT TAA        TCTATGTTGCTCTGTCCTTCGTTGAAATGTTTATGTTTTCTTATTCTGAGGATCATTTGTGTGAGTCGTGTGAAA   +540
AATATTTCAGGTTTTATGTTGGGCTAAGAGGCCTAATGTTTGGGCCCTAGAAATCTGGTTAAACTGTGTAAAGATCTGTTACTTGGTTTAAAGTTTGTG   +640
TGTTTTGTTCACTTCCAAGGAATTTATGTGCAAGAAAGATTAATTGAAAAATTAGCAATAGACTAATGGTTTTATATATTCTATGTTGCAATAAAT     +740
CTTAGGATATGTATATCACTGGAACAGATTCACTATGCCAGTGTGAGAAAGCAATGATAGTTCTAAATCCTCCCAGTCTACTATGCCAATGTTTTAT    +840
AATTTTAATTAATATTTTTATGATGCAATAAGAAAAATTAATGAGACTTTAATAAGAATATATAACAGTCTCAACTAGCATGATCCAACAGCATCGA  3'
```

| Restriction Enzyme | Restriction Site | Restriction Enzyme | Restriction Site |
|---|---|---|---|
| AccI | 278-283 | MboII | 342-346 |
| AhaIII | 113-118 |  | 486-490 |
|  | 189-194 |  | 613-617 |
| AsuI | 271-275 | MnlI | 451-454 |
|  | 311-315 |  | 540-543 |
|  | 665-669 |  | 463-468 |
| AsuII | 339-344 |  | 653-656 |
| AvaII | 311-315 | RsaI | 244-247 |
|  | 665-669 |  | 400-403 |
| AvaIII | 413-418 |  | 438-441 |
| CfrI | 620-624 | ScaI | 437-442 |
| EcoRII | 274-278 | Scr FI | 274-278 |
| FokI | 174-178 | Sfa. NI | 412-416 |
| HaeIII | 272-275 |  | 513-517 |
|  | 621-624 | TaqI | 1-4 |
| Hgi AI | 725-730 |  | 340-343 |
| HinfI | 213-217 |  | 432-435 |
|  | 533-537 |  | 640-643 |
|  | 602-606 |  | 655-658 |
|  |  | XbaI | 83-88 |

HEAT SHOCK PROMOTER AND GENE

Field of the Invention

A class of genes known as heat shock or stress genes occurs in all organisms from bacteria to man. Transcription of these genes is initiated following a stress treatment (e.g., heat shock) and translation of the transcripts produces proteins that probably protect the cell temporarily. During stress, normal polyribosomes quickly break down to monoribosomes which are then used to translate the heat shock mRNA's. Normal mRNA's present before the stress treatment are in some way protected during the stress period and they can be re-used in translation following termination of the stress. The production of heat shock mRNA's and proteins is only a temporary phenomenon and the expression of the heat shock genes levels off after a few hours and then declines. If the temperature is increased slowly rather than in a single step, an organism can withstand temperatures which would otherwise be lethal, i.e., the organism can adapt to higher temperatures.

BACKGROUND OF THE INVENTION

Over two decades ago, it was discovered (Ritossa, F. (1962) Experientia 18:571–573) that specific puffing patterns in the polytene chromosomes of *Drosophila busckii* could be induced by a brief heat shock. The puffing positions of Drosophila species polytene chromosomes are positions where there is active synthesis of mRNA, thus indicating active gene loci (Beerman, W. (1956) Cold Spring Harbor Symp. Quant. Biol. 21:217–232). Since then it has been shown that a variety of agents, e.g., arsenite or anaerobic conditions, can induce responses similar to those induced by heat, suggesting that a more appropriate name for these genes should be "stress genes". However, the nomenclature of "heat shock" genes is now well established and will be used in the remainder of this application.

Since the early 1950's it was known that the pattern of puffs in the polytene chromosomes of Dipteran larvae changed in a regular manner during development, and it was shown that these changes were controlled by ecdysteroid hormones (Clever, U. and P. Karlson (1960) Exp. Cell. Res. 20:623–626; Becker, H.-J. (1962) Chromosoma 13:341–384). In particular, it was shown that the pattern of puffing was disrupted by a brief heat shock (or treatment with certain chemicals) and resulted in the appearance of three new puffs. The induction of these new puffs was very rapid and occurred within minutes of the heat shock treatment, but the induction was transient. For example, when the temperature was raised from 25°→37° C., the puffs reached maximum size within 30 minutes and then regressed. At the same time, all puffs active before the heat shock regressed after the treatment. The heat shock puffing response was also found to occur in all tissues studied and at all stages of development.

It was later found that the heat shock treatment induced synthesis of a small number of polypeptides and repressed the synthesis of most others (Tissieres, A. et al. (1974) j. Mol. Biol. 84:389–398) and the mRNA produced at the new heat shock induced puffs was shown to code for the newly induced polypeptides (Lewis, M. J. et al. (1975) Proc. Nat. Acad. Sci. USA 7.2:3604–3608).

Within a few minutes of heat shock, all polyribosomes break down and are quickly replaced by a new polyribosome peak which contains heat-shock protein mRNA. This mRNA has been hybridized back to the heat shock induced puffs and has been translated in vitro into heat shock proteins (McKenzie, S. et al. (1977) J. Mol. Biol. 117:279–283; Mirault, M. E. et al. (1978) Cold Spring Harb. Syrup. Quant. Biol. 42:819–827). It is of interest to note that even though all polyribosomes break down and the newly induced hs-mRNA's are selectively translated, most normal mRNA's persist during heat shock (Ashburner, N. and J. F. Bonner (1979) Cell 17:241 ff.)

Most of the early work on heat shock genes was done with Drosophila species. However, in 1978, analogous stress responses were found in chick embryonic fibroblasts (Kelly, P. and M. J. Schlesinger (1978) Cell 15:1277–1286), in Chinese hamster ovary cells (Bouche, G. et al. (1979) Nucleic Acids Research 7:1739–1747), in *Escherichia coli* (Lemeaux, P. G. et al. (1978) Cell 13:427–434), in yeast (Miller, M. J. et al. (1979) Proc. Nat. Acad. Sci. USA 76:5222–5225), in Naegleria (Walsh, C. (1980) J. Biol. Chem. 225:2629–2632), in Tetrahymena (Fink, K. and E. Zeutheu (1978) ICN-UCLA Symp. Mol. Cell. Biol. 12:103–115) and in many other species, Including plants (Barnett, T. et al. (1980) Dev. Genet. 1:331–340). A similar pattern of heat shock protein synthesis has also been reported for tobacco and soybean cells growing in solution culture (Barnett, T., et al. (1980) supra) as that reported for soybean seedling tissue. It was also shown that the effects of trauma on vertebrate cells was similar to the effects of heat shock (Hightower, L. E. and F. P. White (1981) J. Cell. Physiol. 108:261).

The transcriptional and translational control of heat shock genes may be autoregulatory. Thus the activity of these genes may be controlled by the concentrations of the heat shock proteins present in the cells. Therefore, inducers of heat shock genes would be factors that either destroyed the heat shock proteins or rendered them to be effectively unavailable within the cell, e.g., by binding to various cell organelles.

The activation and subsequent repression of heat shock genes in Drosophila has been studied by the introduction of cloned segments into Drosophila cells. The P-element-mediated transformation system, which permits introduction of cloned Drosophila genes into the Drosophila germline, was used (Rubin, G. M. and A. C. Spradling (1982) Science 218:348–353). A gene integrated in this way is often present as a stable, single copy and has a relatively constant activity at a variety of chromosomal locations (Scholnick, S. B. et al. (1983) Cell 34:37–45; Goldberg, D. et al. (1983) Cell 34:59–73; Spradling, A. C. and G. M. Rubin (1983) Cell 34:47–57). In particular the Drosophila hsp70 gene was fused in phase to the *E. coli* β-gal actosidase structural gene, thus allowing the activity of the hybrid gene to be distinguished from the five resident hsp70 heat shock genes in the recipient Drosophila. Drosophila heat shock genes have also been introduced and their activity studied in a variety of heterologous systems, and, in particular, in monkey COS cells (Pelham, H. R. B. (1982) Cell 30:517–528; Mirault, M.-E. et al. (1982) EMBO J. 1:1279–1285) and mouse cells (Corces, V. et al. (1981) Proc. Nat. Acad. Sci. 78:7038–7042).

The hybrid hsp70-lacZ gene appeared to be under normal heat shock regulation when integrated into the Drosophila germ line (Lis, J. T. et al. (1983) Cell 35:403–410). Three different sites of integration formed large puffs in response to heat shock. The kinetics of puff formation and regression were exactly the same as those of the 87C locus, the site from which the integrated copy of the hsp70 gene was isolated. The insertion of the 7 kilobase E. coli β-galactosidase DNA fragment into the middle of the hsp70 structural gene appeared to have had no adverse effect on the puffing response. The β-galactosidase activity in the transformants was regulated by heat shock.

Deletion analysis of the Drosophila hsp70 heat shock promoter has identified a sequence upstream from the TATA box which is required for heat shock induction. This sequence contains homology to the analagous sequence in other heat shock genes and a consensus sequence CTxGAAxxTTCxAG has been constructed (Pelham, H. R. B. and M. Bienz (1982) EMBO J. 1:1473–1477). When synthetic oligonucl eotides, whose sequence was based on that of the consensus sequence, were constructed and placed upstream of the TATA box of the herpes virus thymidine kinase gene (tk) (in place of the normal upstream promoter element), then the resultant recombinant genes were heat-inducible both in monkey COS cells and in Xenopus oocytes. The tk itself is not heat inducible and probably no evolutionary pressure has occurred to make it heat inducible But the facts above indicate that tk can be induced by a heat shock simply by replacing the normal upstream promoter element with a short synthetic sequence which has homology to a heat shock gene promoter.

An inverted repeat sequence upstream of the TATA box is a common feature of many of the heat shock promoters which have been studied (Holmgren, R. et al. (1981) Proc. Nat. Acad. Sci. USA 78:3775–3778). In five of the seven Drosophila promoters, this inverted repeat is centered at the 5'-side of the penultimate A residue of the consensus sequence, but the sequence of the inverted repeat itself is not conserved (Pelham, H. R. B. (1982) Cell 30:517–528). In some cases, however, the inverted repeat sequence occurs upstream from the TATA box and the consensus sequence is not present. In these cases there is no heat inducibility so the presence of the inverted repeat does not substitute for the consensus sequence.

The functional significance of the heat shock response is not known. Presumably it functions to protect the cell against the environmental stress and to allow the cell to continue its function after the stress situation has passed. These conclusions are supported by a phenomenon known as "acquired thermotolerance". Cells exposed to a single heat shock, or some other stress, are relatively protected against the effects of a second, otherwise lethal heat shock (Li, G. C. and G. M. Hahn (1978) Nature 274:699–701; Henle, K. J. and L. A. Dethlefsen (1978) Cancer Res. 38:1843–1851; Mitchell, H. K. et al. (1979) Dev. Genet. 1:181–192; McAlister, L. and D. B. Finkelstein (1980) Biochem. Biophys. Res. Commun. 93:819–824).

In higher plants, the heat shock (hs) phenomenon was first discovered at the level of protein synthesis in soybeans (Key, J. L. et al. (1981) Proc. Nat. Acad. Sci. USA 78:3526–3530; Barnett, T. et al. (1980) supra). A number of other plants, e.g., pea, millet, corn, sunflower, cotton and wheat, respond similarly to soybean in that a large number of new proteins of similar molecular weight are induced by a heat shock treatment. The major differences that occur among species are the optimum temperature of induction of hs-proteins, the breakpoint temperature (i.e., above this temperature is lethal), the distribution of the 15–20 kD heat shock proteins on two-dimensional gels and the relative level of normal protein synthesis that occurs during heat shock. It has been shown that an elevation of temperature from 28° C. to 40° C. induced de novo synthesis of several major groups of hs-proteins (hsp) whose molecular weights resemble those found for Drosophila. However, there is a marked difference in the complexity of the low molecular weight (lmw) group of hsp's between these two organisms. Drosophila synthesizes four hsp's of 22, 23, 26 and 27 kilodaltons; soybean produces more than 20 hsp's in the molecular weight range of 15–18 kilodaltons.

The translational preference for hs-mRNA's, while marked, appeared less pronounced in the soybean system (Key, J. L. et al. (1981) supra) than in Drosophila (Storti, R. V. et al. (1980) Cell 22:825–834). The induction of a new set of hs-specific mRNA's in soybean was suggested by in vitro translation of poly(A)+ RNA. Additional evidence for the existence of novel RNA in heat stressed plants was provided by sucrose gradient analysis which showed the accumulation of a $0.49 \times 10^6$ dalton RNA during hs of tobacco and cowpea leaves (Dawson, W. O. and G. L. Grantham (1981) Biochem. Biophys. Res. Commun. 100:23–30). In Drosophila, where transcriptional control of hs protein synthesis is evident, attempts have been made to find signal structures for coordinate expression of these genes (Holmgren, R. et al. (1981) Proc. Nat. Acad. Sci. USA 78:3775–3778). The influence of hs on poly(A)+ mRNA's of soybean has been assessed using cDNA/poly(A)+ RNA hybridization and cloned cDNA/northern blot hybridization analyses (Schoffl, F. and j. L. Key (1982) J. Mol. Appl. Genet. 1:301–314). The hs response in soybean is characterized by the appearance of a new highly abundant class of poly(A)+ RNA's consisting of some twenty different sequences of an average length of 800 to 900 nucleotides and a decrease in total poly(A)+ RNA complexity associated with changes in relative abundance of the 28° C. sequences. The poly(A)+ RNA's of this new abundant cl ass are present at some 15,000 to 20,000 copies per cell after 2 hours of hs at 40° C. The genes for these four Drosophila hsp's comprise a small hs-gene family with similar sequences which are also related to that of α-crystallin (Ingolia, T. D. and E. A. Craig (1982) Proc. Nat. Acad. Sci. USA 79:2360–2364) implying that certain structural domains (possibly for functional aggregation) are shared by these proteins. The lmw-hsp genes in soybeans are the most actively expressed and coordinately regulated genes under hs conditions (Schoffl, F. and J. L. Key (1982) J. Mol. Appl. Genet. 1:301–314). Their hsp's are commonly associated with purified nuclei at high temperature, however, and disaggregate at low temperature (Key, J. L. et al. (1982) In: Schlesinger, M. J., Ashburner, M. and A. Tissieres (eds.) Heat shock, from Bacteria to Man. Cold Spring Harbor Laboratory, pp. 329–336). This indicates a common function for these proteins in hs-response which is possibly related to common structural features in proteins and genes. The lmw-hsp genes are subdivided into eight classes defined by sequence homologies among poly(A)+ mRNA's. Two of the eight classes are particularly interesting with respect to gene expression, because they represent the extreme components of the lmw-hsp genes. These are designated classes I and II; I consists of 13 closely related hsp's genes, while II comprises only lhsp which has no known sequence homology to other hs-genes. Later information showed that class II could be grouped with class I. The separation into the two classes was originally made on the basis of a probe distal to the 3'-translated end of pE2019.

A wide range of crop plants respond to elevated temperatures of heat shock conditions by synthesizing a large number (30 or more) of hs-proteins (Key, J. L. et al. (1983) Current Topics in Plant Biochemistry and Physiology, eds. D. D. Randall, D. G. Blevins, R. L. Larson and B. J. Rapp. Vol. 2, Univ. of Missouri, Columbia, pp. 107–117). The high molecular weight hs-proteins were electrophoretically similar among the species. The more complex pattern of low molecular weight (15–27 kd) hs-proteins showed much more electrophoretic heterogeneity between species. Certainly a given soybean hs-cDNA clone showed greater cross hybridization to different soybean hs-poly(A) RNA's than to any hs-RNA from other species, and this limited hybridization with other species was consistent with the observed electrophoretic heterogeneity of the low molecular weight hs-proteins.

The evolutionary conservation of the hs-response across the spectrum of organisms from bacteria to man suggests an essential function(s) for the hs-proteins. Empirically, one function is to provide thermal protection or thermotolerance to otherwise non-permissive hs temperature (Schlesinger, M. et al. (1982) Heat shock from bacteria to man. Cold Spring Harbor Laboratory, Cold Spring Harbor, N.Y. p.329). Apparently those hs-proteins which are synthesized at a permissive heat shock temperature allow organisms to continue the synthesis of hs-proteins and hs-mRNA's at still higher temperatures and to survive what would be normally lethal temperatures (Key. J. L. et al. (1982) In: Heat Shock from Bacteria to Man. M. J. Schlesinger, M. Ashburner and A. Tissieres, eds. Cold Spring Harbor Laboratory, Cold Spring Harbor, N.Y. p.329). A permissive heat shock temperature is defined here as a temperature which is high enough to induce the heat shock response but not high enough to be lethal. Temperatures above break point temperature are lethal for plants which have not acquired a thermotolerance. In soybean the break point temperature is about 40° C. It has previously been shown that soybean seedlings survive incubation at a lethal temperature by prior incubation at a permissive hs-temperature (Key, J. L. et al. (1983) In: NATO Advanced Studies Workshop on Genome Organization and Expression in Plants. L. Dure, ed. Plenum Press).

Several different treatment regimes of permissive heat shock result in the development of thermotolerance in the soybean seedling. These treatments include: (a) a 1- to 2-hour continuous heat shock at 40° C. followed by a 45° C. incubation; (b) a 30-minute heat shock at 40° C. followed by 2 to 3 hours at 28° C. prior to the shift to 45° C.; (c) a 10-minute heat shock at 45° C. followed by about 2 hours at 28° C. prior to the shift to 45° C.; and (d) treatment of seedlings with 50 ρM arsenite at 28° C. for 3 hours or more prior to the shift to 45° C. The important feature which these treatments have in common is the induction of synthesis and accumulation of heat shock proteins prior to incubation at the potentially lethal temperature. In fact, it has been shown that both hs-mRNA and hs-protein synthesis do occur at 45° C. if the seedlings had earlier been exposed to one of the conditions described above. A likely role(s) for the hs-proteins is to protect vital functions and structures (e.g., transcription, translation and the machinery of energy production) during heat shock and to permit normal functions to return rapidly when favorable temperatures are re-established. It is known that recovery of normal mRNA and protein synthesis occurs rapidly when the temperature is shifted back to normal (e.g., 28° C.) (Key, J. L. et al. (1981) Proc. Nat. Acad. Sci. USA 78:3526–3530; Schlesinger, M. J. et al. (1982) Trends Blochem. Sci. 1:222–225). The resumption of normal protein synthesis utilizes mRNA's conserved during heat shock as well as that newly synthesized during recovery, and there is no detectable synthesis of heat-shock proteins after 3–4 hours at the normal temperature. However, those heat shock proteins that were synthesized during the 40° C. heat shock (recognized by the incorporation of $^3$H-leucine) are very stable during a subsequent chase in non-radioactive leucine, regardless of whether the chase is accomplished at 28° C. or 40° C.; approximately 80% of the label is retained in the heat shock proteins during a 20-hour chase.

The acquisition of thermotolerance appears to depend not only upon the synthesis of heat shock proteins but also on their selective cellular localization. In soybean seedlings, several hs-proteins become selectively localized in or associated with nuclei, mitochondria and ribosomes in a state that causes them to isolate in gradient-purified fractions of these organelles. Specifically, the complex group of 15–18 kilodalton hs-proteins selectively localize in these fractions during heat shock of soybean seedlings. The selective localization of hs-proteins is temperature dependent. The hs-proteins (except the 22–24 kd. hs-proteins which attach to the mitochondrial fraction) chase from the organelle fractions during a 4-hour incubation at 28° C. and they remain organelle associated during a chase at heat shock temperature. In addition, a second heat shock following a 4-hour 28° C. chase results in rapid (within 15 minutes) reassociation of hs-proteins with the organelle fractions. This association of heat shock proteins with nuclei could be explained by the hs-proteins becoming "chromatin proteins" or possibly a part of the matrix structure; both suggestions have been offered following localization studies in the Drosophila system (Arrigo, A. P. et al. (1980) Dev. Biol. 78:86–103). These findings are in basic agreement with autoradiographic results which localized hs-proteins to interband regions of polytene chromosomes (Velazquez, J. et al. (1980) Cell 20:679–689 and (1984) Cell 36:655–662).

Most of the heat shock work in plants has been done with etiolated seedlings, largely due to ease of manipulation. Heat shock proteins have not been extensively analysed in the green tissues of normal plants, but it has been shown that hs-mRNA's accumulate in green leaf tissue to levels similar to those of etiolated seedlings. Additionally, most experimental work has been done using a large temperature shift of about 10° C. The response to such a non-physiological shift, however, is mimicked both at the level of hs-mRNA and hs-protein synthesis and accumulation, by a gradual increase from 28° C. to 47.5° C. in the case of soybean. Thus, the results from what may appear to be non-physiological experiments can be duplicated with etiolated seedlings and green plants under more normal physiological conditions of heat shock, which indeed probably occur in the normal plant environment.

SUMMARY OF THE INVENTION

Four heat shock genes of soybeans have been cloned and sequenced. The heat shock promoter fragments of these four heat shock genes have been subcloned and have been genetically engineered into a T-DNA shuttle vector. These recombinant DNA fragments, i.e., a vector linked to a T-DNA shuttle vector containing a soybean heat shock gene promoter, can then be transferred with the aid of a helper plasmid into *Agrobacterium tumefaciens* where the recombinant DNA fragment is integrated into the Ti-plasmid. The T-DNA portion of the Ti-plasmid can then be transferred to a plant genome, thus allowing transformation of the plant.

Since the heat shock gene promoter is also transferred to the plant genome and is activated temporarily after a heat shock or stress treatment, it is useful to incorporate foreign genes into the recombinant DNA plasmids in such a position as to be expressible under the control of the heat shock gene promoter. Such incorporated foreign genes can be utilized to recognize plant cells transformed by T-DNA or can be activated temporarily. Such temporary activation is useful in the production of the crystalline toxin of *Bacillus thuringiensis*, the production of herbicide resistance or induction of resistance to pathogens.

BRIEF DESCRIPTION OF THE DRAWINGS

FIG. 1 shows the restriction sites and nucleotide sequence of pE2019.

FIG. 2 shows the restriction map of the 7 kilohess HindIll fragment of pE2019.

FIG. 3 shows the nucleotide sequences and consensus sequences of promoters from different heat shock genes.

FIG. 4 shows the nucleotide sequences of the coding regions from different heat shock genes.

FIG. 5 shows the nucleotide sequences of the 3′ non-coding regions from different heat shock genes.

FIG. 6 shows the construction of a pBR322-based plasmid containing the beta-galactosidase gene under the control of a soybean heat shock promoter.

FIG. 7 shows the construction of a plasmid containing $T_L$-DNA and a genetic construct comprising the beta-galactosidase gene under the control of a soybean heat shock promoter.

FIG. 8 shows the construction of a Ti-plasmid containing a genetic construct comprising the beta-galactosidase gene under the control of a soybean heat shock promoter.

FIG. 9 shows the nucleotide sequence and restriction sites of hsp6871.

DETAILED DESCRIPTION OF THE INVENTION

Chromosomal DNA isolated from purified nuclei of soybeans was subjected to restriction enzyme analysis and southern blot hybridizations using cloned hs-cDNAs as hybridization probes. Six sets of cDNA clones which reflected members of "different" multigene families for hs proteins ranging from 15 to 27 kD (there are at least 30 hs proteins in plants within this size range) have been identified. In addition, one gene clone (hs6871) was isolated by use of cDNA clone 1968 as a probe. These groups are as follows:

TABLE 1

| | Classification of heat shock gene families in soybeans*** | | |
|---|---|---|---|
| cDNA clone | Number of Clones by Hybrid Selection | Translation of hs mRNAs | Heat shock promoter fragment |
| pFS2005* | 13 | 15–18 kD hs proteins | hsp2005 |
| pFS2019** | 1 | 18 kD hs protein | hsp2019 |
| pCE53* | 13 | 15–18 kD hs proteins | hsp53 |
| pCE75 | 8 | 15 kD hs proteins | hsp75 |
| pCE54*** | 4(5) | 27 kD hs proteins | hsp54 |
| pFS2033 | 3 | 20–24 kD hs proteins | hsp2033 |
| hs6871 (gene clone) | 1 | 17.3 kD hs protein | hsp6871 |

*These and several other cDNA clones reflect members of the same multi-gene family.
**May reflect also a "unique" cDNA clone to the same multigene family represented by pFS2005 and pCE53.
***The expression of these heat shock gene families is induced following many other stress treatments, e.g., treatment with arsenite.

A major effort has been devoted to isolating, restriction mapping, subcloning and sequencing genomic clones isolated from a λ 1059 soybean library (constructed by the Agrigenetics Advanced Research Laboratory, Madison, Wis.), and to DNA sequence analysis of the cDNA clones described above.

Four subclones, namely pE2019, pL2005, pM2005 and hs6871 were generated from λ genomic clones and were sequenced. These four subclones represent three different gene families, i.e., cDNA clones 2005, 2019 and 1968. EcoRI fragments were selected on the basis of their homology to cDNAs from these genomic clones and were subcloned into pUC9. Sequence analysis was done on parts of these inserts, i.e., 856 nucleotides of pE2019 (FIG. 1), 971 nucleotides of pL2005, 944 nucleotides of pM2005, and 1536 nucleotides of hs6871, respectively. Sequence homology analysis has located the corresponding cDNA homology within each of the genomic subclone sequences. Cross-homology analysis showed substantial cDNA homology among the genomic subclones: (a) pe2019 corresponds to greater than 98% homology over the 340 bases of pFS2019 cDNA clone (b) immediately upstream from This 2019 homology is a region which shows over 90% homology to the pCE53 cDNA clone sequence of 350 bases. Therefore sequence data and hybrid selection/translation data indicate that pCE53 is a member of the pFS2005 gene family (see Table 1 above) (c) Additionally, pFS2019 was found to be a 3′-nontranslated region of a member of the 2005 gene family. (d) Homology matrix analysis has shown that even cDNAs that do not cross hybridize (e.g., pCE75 and pFS2033) contained long stretches of greater than 50% homology with 70% homology over lengths of up to 40 nucleotides.

A 7 kilobase HindIII fragment (H2) (FIG. 2) of the soybean genomic clone pe2019 that hybridizes to the cDNA 2019 has been identified. The pe2019 gene was mapped to the left terminal BamHI subfragment (designated BH—FIG. 2) of H2 since This region was shown to be the only portion hybridizing to the cDNA 2019 probe. This fragment was selected for sequencing studies and for introduction into the Ti-plasmid. Using the M13 kilodeletion strategy (Barnes, W. M. and M. Bevan (1983) Nucleic Acids Research 11:349–368) fragment BH has been sequenced and a series of deletion phages spanning This subfragment have been constructed. Of interest are several regions showing 78% homology with the Drosophila heat shock consensus sequence (CTxGAAxxTTCxAG) (FIG. 3) and the core (73%) of the SV40 base pair repeat (GGTGTGGAAAG) (FIG. 3).

The polarity of the transcript and the position of the cDNA homology on H2 (see FIG. 4 for coding sequence) demonstrated that the promoter to gene 2019 is situated on H2 about one hundred and ninety base pairs to the right of the BamHI site of subfragment BH. The polarity of the 2019 gene is 5'- to 3'-from one hundred and fifty seven nucleotides upstream from the leftmost BamHI site of H2 toward the left HindIII site. This conclusion is based on the hybridization of M13 single stranded probes and S1 hybrid protection studies with soybean heat shock RNA. The 5'-termini of all three genes are positioned from 32 to 28 bases from the first T of a "TATA" motif (the TTAAATAC) suggesting that this region functions as the promoter. Northern blot analysis and S1 hybrid protection results using heat shock RNA showed that the transcript was from 680–900 bases in length excluding the poly(A) tail which was shown to be approximately 150 bases in length. Since the cDNA was less than full length (ca. 350 bases) and was obtained by priming with oligo-dT, it therefore represents the 3'-portion of the transcript. Therefore, from the position of the cDNA homology on the BH fragment, the transcript must extend 3'- to 5'- from position 590 towards the BamHI site and beyond. This conclusion was confirmed by S1 hybrid protection mapping using 3'-labelled BH fragment. A protected band of 590±10 base pairs was seen which agreed with the 3'-end of cDNA homology and showed that the 5'-terminus and promoter lay to the right of the BamHI site.

Figure 5:
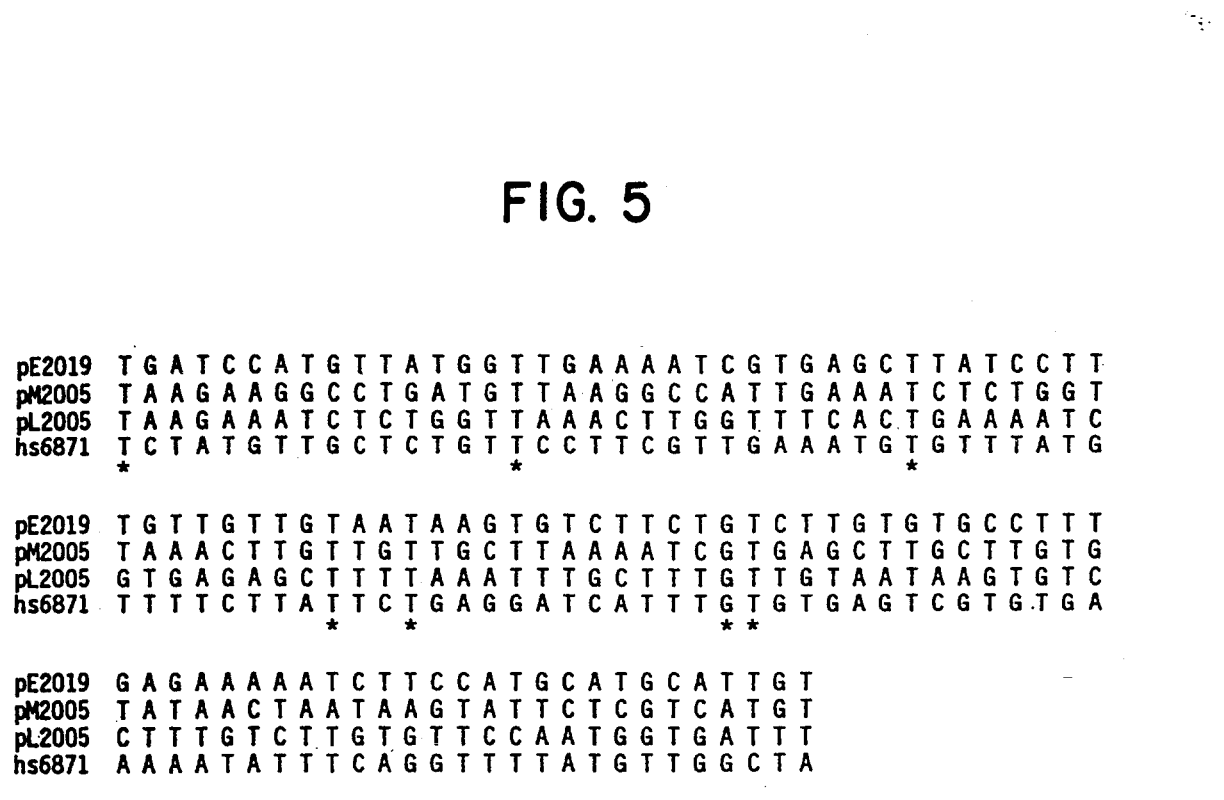

The coding sequence of clone pe2019 has been completed (FIG. 4). It consists of an open reading frame of 462 nucleotides. In addition, 291 nucleotides on the 5'-side (i.e., upstream) of the ATG translation initiation codon have been sequenced. These 291 nucleotides include all the essential elements of a promoter region, i.e., CAAT box, TAATA box and transcription initiation. In addition, there is a "consensus sequence" (131–144 nucleotides upstream from the ATG translation initiation codon with the sequence 5'-CTxGAAxxTTCxAG-3') which has been found in all heat shock gene and is required for heat induction (Pelham, H. R. B. and M. Bienz (1982) EMBO J. 11:1473–1477). If this consensus sequence has been deleted from the promoter region, then the heat shock gene is not induced following the stress of a heat shock or any other stress. Another sequence which has a high homology to the SV-40 enhancer sequence occurs at 172 to 185 nucleotides upstream from the translation initiation codon but, at present, the significance of this discovery is not obvious. A conserved sequence is present far upstream and this sequence is also found in an analogous position in two Drosophila heat shock promoters. Finally, the sequence of 731 nucleotides on the 3'-side (i.e., downstream) from the TGA stop codon has been elucidated (part of this sequence is shown in FIG. 5).

The coding sequences and flanking sequences of three other heat shock genes (i.e., clones pM2005, pL2005 and hs6871) have been determined. In the case of pM2005, an open reading frame of 423 nucleotides (FIG. 4) has been determined as well as 418 nucleotides upstream (and including all the promoter regulatory sequences described for pe2019 in the previous paragraph) from the ATG translation initiation codon (FIG. 3) and 171 nucleotides downstream from the TAA stop codon (100 nucleotides shown in FIG. 5). In the case of pL2005, an open reading frame of 450 nucleotides (FIG. 4) has been determined as well as 422 upstream (FIG. 3) (and including all the promoter regulatory sequences described for pe2019 in the previous paragraph) from the ATG translation initiation codon and 842 nucleotides downstream from the TAA stop codon (100 nucleotides shown in FIG. 5). In the case of hs6871, an open reading frame of 459 nucleotides (FIG. 4) has been determined as well as 456 upstream (FIG. 3) (and including all the promoter regulatory sequences described for pe2019 in the previous paragraph) from the ATG translation initiation codon and 943 nucleotides downstream from the TAA stop codon (100 nucleotides shown in FIG. 5).

These four heat shock genes have substantially homologous sequences in the coding regions (FIG. 4). In the upstream promoter regions (FIG. 3) the clones pe2019, pM2005 and pL2005 have substantially homologous sequences, but there are many differences between the nucleotide sequences of these three clones and that of hs6871. However, it should be noted that there are strong similarities between the "heat shock consensus sequences" of all four clones, i.e., CTxGAAxxTACxxx (FIG. 3). The data for 100 nucleotides on the downstream of the stop codons for the four sequences are given (FIG. 5). It is obvious that very little sequence homology occurs. Significantly, the coding sequences, the upstream promoter regions (i.e., 5'- to the translational initiation codon) and the downstream flanking region (i.e., 3'- to the stop codon) of these four soybean heat shock genes have almost no resemblance to the corresponding regions of Drosophila heat shock genes (Hacket, R. W. and J. T. Lis (1983) Nucleic Acids Res. 11:7011–7030; Ingolia, T. D. and E. A. Craig (1982) Proc. Nat. Acad. Sci. USA 79:2360–2364; Southgate, R. et al. (1983) J. Mol. Biol. 165:35–67). Although there are similarities between the "consensus sequences" of the promoter regions from Drosophila and soybean heat shock genes, the promoter regions of soybean heat shock genes do not possess the inverted repeat sequences characteristic of the Drosophila genes.

The promoter regions of the soybean heat shock genes can be utilized in a number of ways whenever a transitory activation of a foreign gene or a soybean gene is required. [A foreign gene is herein defined as any gene normally found in the genome of any species other than a soybean.] For example, when the T-DNA from a wild type Ti-plasmid of *Agrobacterium tumefaciens* is transferred to a plant genome, then the resultant transformed plant cells are tumorous. These transformed tumorous plant cells in tissue culture cannot be used to regenerate intact whole plants. On the other hand, if a "disarmed" T-DNA region is used, then intact whole plants can be regenerated from transformed plant cells in tissue culture, but it is difficult to differentiate between transformed and untransformed cells. In the present invention this difficulty is overcome by placing the β-galactosidase gene of *E. coli* under the heat shock inducible control of a soybean heat shock gene promoter. This recombinant construction comprises the soybean heat shock promoter region and the coding region for the 24 codons at the 5'-terminus of the heat shock gene (see Example 5). This recombinant DNA fragment is then integrated into the T-DNA of a Tiplasmid and used to transform plant cells. In the presence of a suitable substrate, transformed cells in tissue culture can then be differentiated from untransformed cells by the development of a blue color following a heat shock treatment. Thus the β-galactosidase-heat shock promoter combination is used as a means of recognizing transformed plant cells. This invention is not limited to the β-galactosidase gene example and will include other genes which could be useful in the recognition of specific plant cell types when such genes are placed under the control of a plant heat shock gene promoter. Such genes useful in the recognition of transformed plant cells are defined herein as transformation recognition genes.

In a second example it will be useful to follow the protocol outlined above except that a gene which one wishes to be transitorily expressed is placed under the control of the soybean heat shock promoter. This recombinant construction comprises only the soybean heat promoter region, i.e., 159 nucleotide pairs extending from the AluI site (17 base pairs upstream from the ATG translation initiation codon) to the EcoRI site (176 base pairs upstream from the ATG translational initiation site) (see Example 7). If genes coding for insecticidal proteins (including but not limited to the crystalline endotoxin of Bacillus thuringiensis are placed under the control of a plant heat shock gene promoter, then it will be possible to activate expression of the insecticidal proteins during the heat of the day. This period coincides with the eating period of insect larvae and thus confers insect resistance to the plant—but only for a limited, critical period during each day. Similarly, if a gene conferring herbicide resistance is placed under the control of a heat shock promoter, then it is possible to spray the fields with herbicide after the herbicide resistance gene has been activated during the heat of the day.

EXAMPLE 1

Plant material used and heat shock conditions

Soybean seeds (Glycine max variety Wayne) were germinated in moist vermiculite in the dark at 28°-30° C. for 3 days. After This time plants were sprayed with $2 \times 10^{-3}$M 2,4-dichlorophenoxyacetic acid, and mature hypocotyl tissue was harvested 24 hours later. The tissue was incubated in a buffer containing 1% sucrose, 1 mM K-phosphate (pH 6.0), 50 µg/ml chloramphenicol, 10 µg/ml 2,4-dichlorophenoxyacetic acid at 28° C. (control) or at 40° C. and 42.5° C. (heat shock), respectively, for two hours unless stated differently.

EXAMPLE 2

Purification of poly(A)+ RNA and construction of cDNA recombinant clones

Total RNA was extracted from hypocotyl tissue after incubation (see Example 1), and poly(A)+ RNA was purified as described (Silflow, C. D. et al. (1979) Biochemistry 13:2725-2731) with modifications (Key, J. L. et al. (1981) Proc. Nat. Acad. Sci. USA 78:3526-3530). Poly(A)+ RNA from hs soybean hypocotyl was used as a template for oligo-(dT)-primed double stranded cDNA synthesis (Wickens, M.P. et al. (1978) J. Biol. Chem. 253:2483-2495; modified by Baulcombe, D. C. and J. L. Key (1980) J. Biol. Chem. 255:8907-8913). As a further modification, the synthesis of the first strand was unlabelled and 20 µM [$^{32}$P]dCP (400 Ci/mM, Amersham) was used as a tracer for second strand synthesis by DNA polymerase I (Boehringer Mannheim). The S1-digested double stranded cDNA was size fractionated on a 10–30% sucrose gradient in 10 mM Tris-HCl pH 7.5, 1 mM EDTA and 100 mM NaCl, run at 50,000 rpm for 6 hours at 20° C. in a Beckman SW 50.1 rotor. About 0.5 µg double stranded cDNA (of length greater than 500 bp) was subjected to homopolymer tailing, adding poly(dC) to the 3'-ends of fragments by terminal transferase (Bethesda Research laboratories) (Roychoudhury, R. and R. Wu (1980) In: Grossman, L., Moldave, K., eds. Methods in Enzymol. Vol. 65; New York: Academic Press, pp. 43-62). An average length of 30 nucleotides/end was synthesized. In an analogous reaction 1 µg of PstI cut pBR322 was tailed with poly(dG) to the same extent. In an annealing reaction 0.7 µg (dG)-tailed pBR322 and 0.14 µg (dC)-tailed cDNA were used. Annealed molecules were used to transform *Escherichia coli* SK1590 (Kushner, S. R. (1978) In: Boyer, H. W., Nicosia, S. eds. Genetic Engineering, Amsterdam: Elsevier/North Holland Biomedical Press, pp. 17-23). Transformants were selected on tetracycline-containing medium, 99% of which carried recombinant plasmids as indicated by their TcRApS phenotype.

EXAMPLE 3

Screening of a soybean genomic DNA library

High molecular weight DNA was isolated from purified nuclei essentially as described (Nagao, R. et al. (1981) DNA 2:1-9). Screening of a soybean genomic DNA library, cloned into the EcoRI site of a λ Charon 4A vector was carried out as described (Nagao, R. T. et al. (1981) DNA 1:1-9), using radioactively labelled insert probes of cDNA clones which had been synthesized from poly(A)+ RNA of heat shock treated soybean hypocotyls (Schoffl, F. and J. Key (1982) J. Mol. Appl. Genet. 1:301-314).

EXAMPLE 4

Restriction endonuclease digestion and Subcloning of DNA fragments in pBR322

Assay conditions for DNA digestions with the restriction endonucleases EcoRI, HindIII and PstI were as described (Maniatis, T. et al. (1982) Molecular cloning, a Laboratory Manual, Cold Spring Harbor Laboratory) and standard electrophoresis of DNA fragments on 1% agarose gels was also as described (Schoffl, F. and A. Puhler (1979) Genet. Res. Camb. 34:287-301). Ten µ g/lane was applied for soybean chromosomal DNA digests and about 0.5 µg/lane for plasmid or λ-DNA digests. Completion of digestion was tested for soybean chromosomal DNA by southern blot hybridization with soybean rDNA probes (kindly provided by Dr. R. Nagao, University of Georgia). Fragment sizes were generally determined by comparison with X-DNA digests (EcoRI, HindIII, EcoRI/HindIII) run on the same gel. Subcloning of EcoRI/HindIII fragments of genomic soybean DNA into the respective sites of pBR322 was carried out as described (Maniatis, T. et al. (1982) supra). Potential recombinant clones were screened by sizing the cloned DNA fragments on agarose gels using restriction fragments of a standard heat shock gene (λhs68-7) as a reference. Specific clones were identified by southern blot hybridization using cDNA probes of clone 1968 (Schoffl, F. and J. L. Key (1982) J. Mol. Appl. Genet. 1:301-314).

EXAMPLE 5

Construction of a recombinant plasmid containing the β-galactosidase gene inserted into the coding region of soybean heat shock gene 2019

Figure 6:
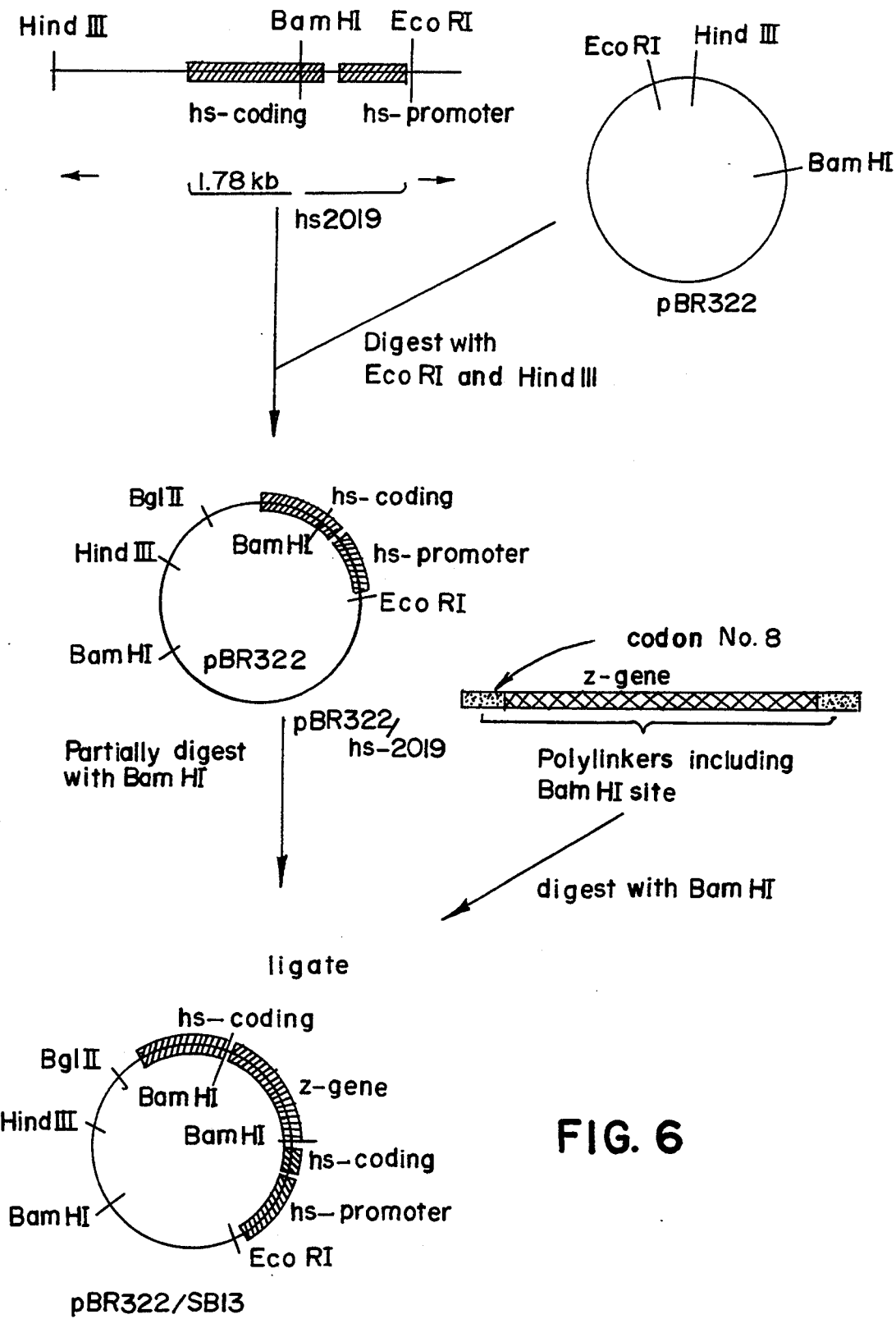

The starting material for this construction (defined here as a recombinant soybean heat shock gene) is the 7 kilobase (kb) HindIII fragment (H2) containing the promoter of heat shock gene 2019, the coding sequence of the same heat shock gene and a flanking sequence on the 3'-side of the reading strand of this coding sequence (referred to hereafter as hs2019) (FIG. 6). This H2 sequence is digested with the restriction endonuclease EcoRI and the products are separated by electrophoresis on agarose gel. The 1.78 kb HindIII-EcoRI which contains all the components of heat shock gene 2019 is then inserted into plasmid pBR322 previously cleaved with HindIII and EcoRI. This recombinant plasmid (pBR322-hs2019) is then transformed into *E. coli* JM101 where it is amplified. Following amplification, pBR322-hs2019 is partially cleaved with BamHI and a Z gene (coding for β-galactosidase) carrying polylinkers at both ends (Casadaban, M. J. et al. (1983) Methods Enzymol. 100:293-308) is inserted into the hs2019 BamHI site. The polylinkers on each end of the Z-gene are previously cleaved with BamHI. It should be noted that the Z-gene may also insert into the BamHI site of pBR322. Insertion at the two sites can be differentiated by restriction mapping. The BamHI site of the hs2019 gene is at codon 24 of the hs2019 coding region and this construction thus maintains the coding region of the Z-gene inframe following the first 24 codons of the hs2019 gene. This recombinant soybean heat shock gene inserted into pBR322 is designated hereinafter as pBR322/SB13 (i.e., pBR322 with an hs2019 promoter-24 codons of hs2019 coding sequence-Z-gene-hs2019 coding sequence-3'-flanking sequence). SB13 (referred to hereinafter as a recombinant soybean heat shock gene) can be recovered from pBR322/SB13 by cleavage with HindIII and EcoRI followed by separation of the products by agarose gel electrophoresis.

EXAMPLE 6

Figure 7:
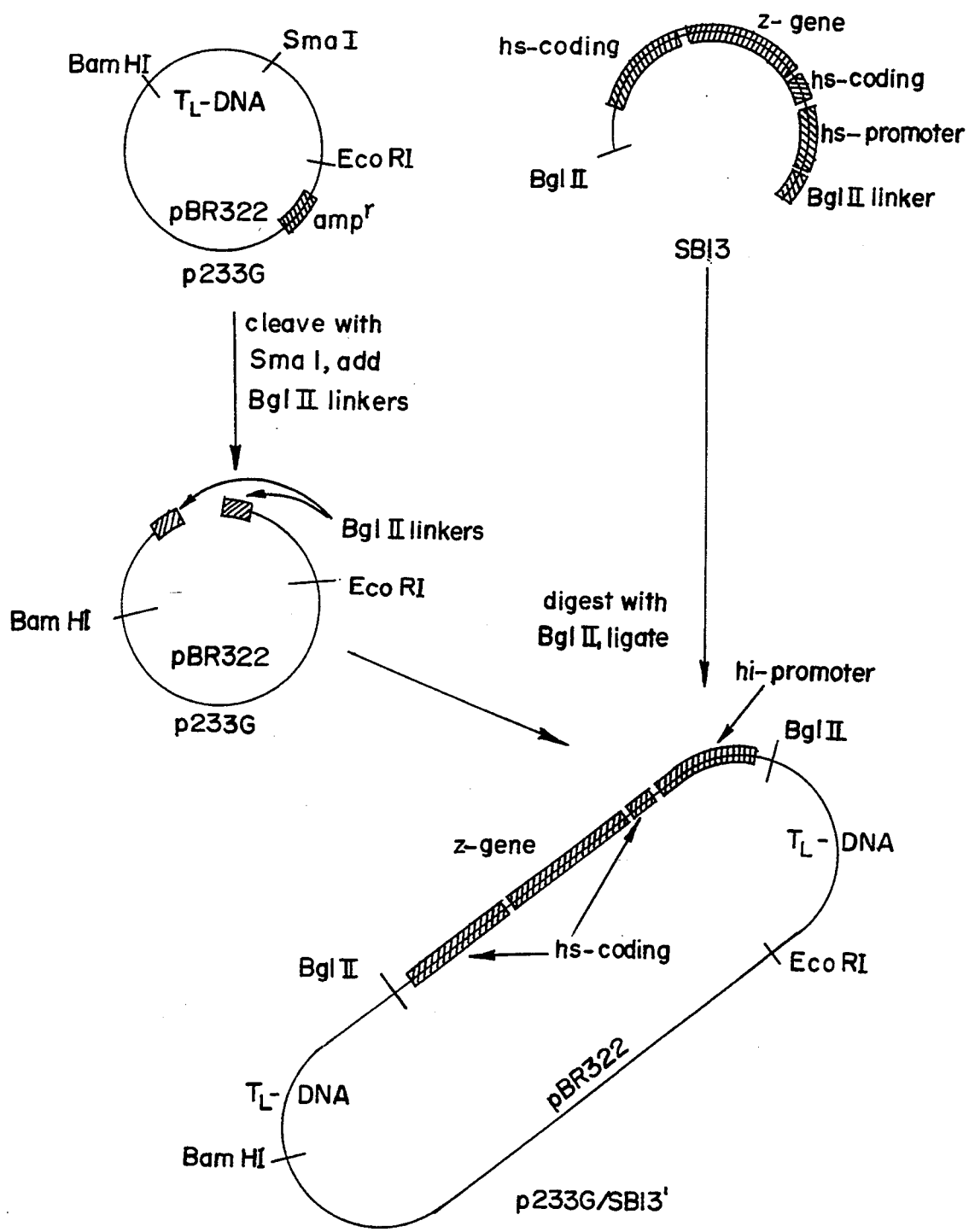

Incorporation of soybean hs-promoter -β-galactosidase-hs coding-hs3'-tail (i.e., SB13) into the Ti-plasmid of Agrobacterium tumefaciens A T-DNA shuttle vector p233G comprising pBR322 and the $T_L$-DNA of the Ti-plasmid of *A. tumefaciens* was obtained from the Agrigenetics Advanced Research Laboratory, Madison, Wis. This T-DNA shuttle vector (p233G) had been transformed into *E. Coli* JM101. pBR322 is resistant to both ampicillin (amp$^r$) and tetracycline (tet$^r$), but p233G is only amp$^r$ because the $T_L$-DNA has been inserted into the tet$^r$ gene, thus destroying its activity (FIG. 7). Following amplification, p233G is purified and cleaved at the SmaI restriction endonuclease site in transcript number 10 of T-DNA from *A. tumefaciens* strain 15955 (Barker, R. F. et al (1983) Plant Mol. Biol. 2:335-350). BglII linkers are then added to this SmaI site and digested with BglII.

Figure 8:
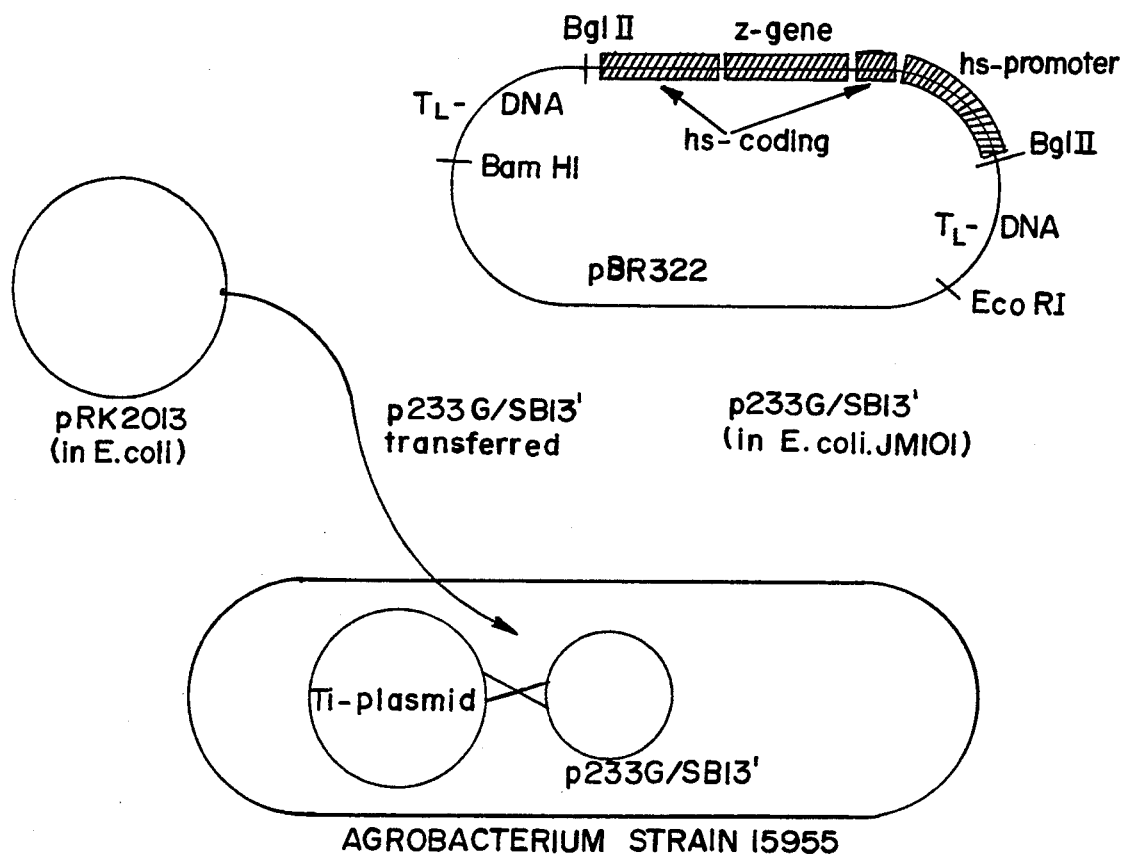

SB13, previously recovered by cleavage of pBR322/SB13 by HindIII and EcoRI, has overhanging single stranded ends produced by the action of these restriction endonucleases. These overlaps are filled in by use of DNA polymerase I (Klenow fragment) and BglII linkers are blunt end ligated (FIG. 7). SB13 is then digested with BglII restriction endonuclease and the BglII fragment is isolated by agarose gel electrophoresis. It will be noted that a BglII restriction site occurs 39 base pairs from the 3'-terminus of the hs2019 mRNA (FIG. 2) and that this BglII site will therefore represent one end of the BglII fragment. For this reason, the nomenclature of the SB13 fragment is altered to SB13'. The BglII fragment is then inserted into the linearized p233G, i.e., the T-DNA shuttle vector, resulting in plasmid p233G/SB13'(defined here as a co-integrated recombinant DNA fragment) and transformed into *E. coli* strain JM101. Following amplification, a triple mating is done using (1) a helper plasmid (pRK2013) in an *E. coli* strain, (2) the plasmid p233G/SB13' in *E. coli* JM101 and (3) strain 15955 of *A. tumefaciens* containing a Ti-plasmid (FIG. 8). Strain 15955 is resistant to streptomycin (str$^r$). pRK2013 and the recombinant shuttle vector p233G/SB13 ' have replication origins which are functional in *E. coli* strains but not in *A. tumefaciens*. Thus a helper plasmid can be defined as a plasmid that promotes transfer of a normally non-transferrable second plasmid from one bacterial strain to another. However, pBR322 has a mobilization site (mob) which is recognized by the transfer gene (tra) of pRK2013 so the recombinant shuttle vector p233G/SB13' can be transferred to *A. tumefaciens*. However, p233G/SB13' cannot replicate in *A. tumefaciens*, so its presence can only be stabilized by recombination (single crossover or double reciprocal crossover) with the resident Ti-plasmid. These three strains are mixed and incubated for 16 hours after which the recombinant resident Ti-plasmid (i.e., Ti-p233G/SB13') is selected by plating for 72 hours on a medium containing streptomycin and carbenicillin. Streptomycin selects the Agrobacterium and carbenicillin selects the pBR322. The recombinant Ti-p233G/SB13' promoter plasmid in *A. tumefaciens* strain 15955 can now be utilized.

The recombinant Ti-p233G/SB13' resident plasmid now contains the β-galactosidase producing gene (i.e., the Z-gene) under the control of the hs2019 heat shock promoter within the T-DNA of the Ti-plasmid in a stable form within *A. tumefaciens* strain 15955. Following infection of a plant or plant cell culture by the bacteria, the T-DNA can be transferred to the plant genome. Plant tissue or plant cells, which have been thus transferred, can then be recognized by the expression of the Z-gene (defined here as a transformation recognition gene) resulting in the production of a blue color after heat treatment in a medium containing 5-bromo-4-chloro-3-indolyl-β-D-galactoside (X-gal) (Miller, J. H. (ed.) (1975) Experiments in Molecular Genetics. Cold Spring Harb. Lab., Cold Spring Harbor, N.Y.). Most important is that the expression of the blue color is only transitory.

EXAMPLE 7

Isolation of the heat shock promoter from heat shock gene 2019 of soybeans and insertion of this heat shock promoter into $T_L$ DNA of plasmid p233G Starting material for the isolation of gene 2019 heat shock promoter is the pUC8-derived clone BE250 (FIG. 2). The plasmid pUC8-BE250 contains the BamHI-EcoRI subfragment of H2 that includes the promoter and part of the coding region of the heat shock gene 2019. This plasmid is digested with restriction endonuclease AluI and the promoter-containing fragment is isolated (FIG. 1). The fragment extends 65 base pairs downstream from the start of transcription to include a major portion of the untranslated leader sequence, but not the start codon for translation. HindIII linkers are blunt-end ligated to the fragment and the ligation product is redigested with HindIII and BamHI before cloning into similarly digested pUC8. Heat shock promoters from all three isolated genes (E2019, M2005, L2005) are cloned in a similar fashion and designated hsprE2019, hsprM2005, and hsprL2005, respectively.

The plasmid p233G is linearized by digestion with BglII and the resulting single-strand end filled in using the Klenow fragment of DNA polymerase I. A synthetic polylinker (5'-GAGATCTAAGCTTCTAGAC-3', double stranded) is ligated into p233G at the filled-in BglII site. This polylinker contains the restriction sites of BGlII, HindIII and XbaI endonucleases, and is used for insertion of both the BamHI/HindIII-flanked promoter fragments and HindIII/XbaI-generated coding region fragments. The coding region fragments can be obtained from any gene as long as the fragments contain no upstream ATG sequences other than the start codon for translation. The coding fragment must also contain an untranslated 3'-tail with a polyA addition site (AA-TAAA) for correct processing of the mRNA.

Such heat shock expression plasmids are then transformed into a strain of *E. coli* , e.g., JM101 or JM103, which will allow replication. Following amplification in such a host strain, the heat shock expression plasmids can be transferred to Agrobacterium strains which can then be used to transform plant cells as already described in Example 6.

EXAMPLE 8

Construction and isolation of a heat shock promoter sequence from the heat shock gene clone phs6871

The isolation of a soybean heat shock gene and the insertion of this gene into pBR322 to give a recombinant plasmid phs6871 have been described (Schoffl, F. and J. L. Key (1983) Plant Mol. Biol. 2:269–278). Following amplification in an *E. coli* K12 strain, the recombinant plasmid is purified and cleaved with a mixture of the restriction endonucleases CfrI and AccI. If the first nucleotide A of the ATG translation initiation codon is numbered +1, then cleavage with these two restriction endonucleases will produce a fragment covering the nucleotides −314 (i.e., 314 nucleotides "upstream" from the above-described A) (FIG. 9). Upstream is defined here as being in the 5'-direction and downstream is in the 3'-direction from the A nucleotide of the ATG translation initiation codon on the reading strand of the DNA. The fragment is then purified and the single stranded overhangs created by the restriction enzymes are blunt-ended by methods well known in the art (Maniatis, T. et al. (1982) Molecular cloning—a laboratory manual. Cold Spring Harbor Laboratory). EcoRI linkers are then added to both ends of the fragment which is then cloned into the EcoRI site of M13mp9. Following transformation into *E. coli* JM103, the cloned fragment is amplified and single stranded templates corresponding to the reading strand of the heat shock gene are packaged and extruded into the media. These single stranded templates are recovered from the supernatant following removal of the bacterial host. A ten-fold excess of a previously constructed synthetic DNA primer mismatched in four base pairs (5'-TTTCCCGGGTCAGTCTTGTG-3') in the presence of the four deoxynucleotide triphosphates (one of which is radioactive) and DNA polymerase I (Klenow fragment) is now used to generate a modified double stranded DNA The four mismatched nucleotides CCGGG are indicated by underlines). The mixture is incubated for a sufficient period at 37° C. to allow two full cycles of replication. The fragment containing the hs6871 promoter region is then isolated and purified following a mixed digestion with the restriction endonucleases EcoRI and SmaI. The overhang generated by the EcoRI digestion is then blunt ended and the fragment (now with both ends blunt) is then blunt end ligated into the SmaI site of p233G and the recombinant DNA plasmids are amplified following transformation into a suitable host. It will be noted that two full cycles of DNA replication starting from the mismatched synthetic DNA primer generates a SmaI restriction site. The fragment containing the hs6871 promoter will be inserted in both orientations into the SmaI site of p233G, but in both orientations a SinaI site is regenerated downstream from the hs6871 promoter sequence and can be utilized for the insertion of foreign genes or soybean genes of interest. In particular, it should be noted that there is NO SmaI site generated upstream from the hs6871 promoter region. As described in Example 7, the p233G constructs containing an inserted heat shock promoter hs6871 are defined as recombinant DNA plasmids. These recombinant DNA plasmids with foreign genes or soybean genes inserted are designated (as in Example 7) as heat shock expression plasmids. Transfer of heat shock expression plasmids into a plant genome is accomplished as described in Example 7.

What is claimed is:

1. A recombinant heat shock gene comprising a plant heat shock promoter and a heterologous structural gene whose expression is controllable thereby, wherein said promoter comprises the consensus nucleotide sequence 5'-C-T-X-G-A-A-X-X-T-A-C-X-X-X-3', where X is A,T,C or G.

2. A recombinant heat shock gene comprising a plant heat shock promoter and a heterologous structural gene whose expression is controlled thereby, wherein said promoter comprises the consensus nucleotide sequence 5'-C-T-S-G-A-A-M-R-T-A-C-W-M-K-3' where S is C or G; M is A or C; R is A or G; W is A or T; and K is T or G.

3. The recombinant heat shock gene of claim 2 wherein said heat shock promoter is derived from soybean.

4. The recombinant heat shock gene of claim 3 wherein said heat shock promoter is a soybean heat shock promoter selected from the group consisting of hsp2005, hsp2019 and hsp6871.

5. The recombinant heat shock gene of claim 2 wherein said heterologous structural gene is a crystalline insect toxin gene of *Bacillus thuringiensis*.

6. The recombinant heat shock gene of claim 2 wherein said heterologous structural gene is a herbicide resistance gene.

7. The recombinant heat shock gene of claim 2 wherein said heterologous structural gene is a Z-gene coding for $\beta$-galactosidase.

8. A vector comprising a fragment of DNA capable of functioning as a plant heatshock promoter wherein said fragment of DNA comprises the consensus nucleotide sequence 5'-C-T-X-G-A-A-X-X-T-A-C-X-X-X-3', where X is A, T, C or G.

9. A vector comprising a fragment of DNA capable of functioning as a plant heat shock promoter wherein said fragment comprises the consensus nucleotide sequence of 5'-C-T-S-G-A-A-M-R-T-A-C-W-M-K-3' where S is C or G; M is A or C; R is A or G; W is A or T; and K is T or G.

10. The vector of claim 9 also comprising a structural gene under the control of said fragment of DNA.

11. The vector of claim 9 which is a plasmid.

12. The plasmid of claim 11 which comprises pBR322 containing said fragment of DNA.

13. The vector of claim 9 comprising said fragment of DNA inserted into a T-DNA fragment of a Ti-plasmid from an Agrobacterium strain.

14. The vector of claim 10 in which said structural gene is a heterologous structural gene.

15. The vector of claim 14 in which said structural gene is a soybean gene.

16. The vector of claim 9 in which said DNA fragment is a plant DNA fragment.

17. The vector of claim 16 in which said fragment of plant DNA is a fragment of soybean DNA.

18. The vector of claim 17 in which said fragment of plant DNA is a soybean heat shock promoter selected from the group consisting of hsp2005, hsp2019 and hsp 6871.

19. A bacterial strain containing therein recombinant DNA comprising:
 (a) a fragment of DNA capable of controlling heat-shock expression of a gene in a plant; and
 (b) a structural gene oriented with respect to said fragment of DNA so as to be expressible under the control thereof
wherein said fragment of DNA capable of controlling heat shock expression of a gene in a plant comprises the consensus nucleotide sequence 5'-C-T-X-G-A-A-X-X-T-A-C-X-X-X-3', where X is A, T, C or G.

20. A bacterial strain containing therein recombinant DNA comprising:
 (a) a fragment of DNA capable of controlling heat shock expression of a gene in a plant; and
 (b) a structural gene oriented with respect to said fragment of DNA so as to be expressible under the control thereof
wherein the fragment of DNA capable of controlling heat shock expression of a gene in a plant comprises the consensus nucleotide sequence 5'-C-T-S-G-A-A-M-R-T-A-C-W-M-K-3' where S is C or G; M is A or C; R is A or G; W is A or T; and K is T or G.

21. The bacterial strain of claim 20 comprising a vector, said vector comprising said recombinant DNA.

22. The bacterial strain of claim 21 wherein said vector is pBR322.

23. The bacterial strain of claim 20 wherein said fragment of DNA is a fragment of plant DNA.

24. The bacterial strain of claim 23 wherein said fragment of plant DNA is derived from soybean DNA.

25. The bacterial strain of claim 24 wherein said fragment of DNA is a soybean heat shock promoter selected from the group consisting of hsp2005, hsp2019 and hsp 6871.

26. The bacterial strain of claim 20 which is *Escherichia coli*.

27. The bacterial strain of claim 20 which is a member of the genus Agrobacterium.

28. The bacterial strain of claim 27 which is *Agrobacterium tumefaciens*.

29. The bacterial strain of claim 27 which is *Agrobacterium rhizogenes*.

30. The bacterial strain of claim 20 wherein said structural gene is a heterologous structural gene.

31. The bacterial strain of claim 30 wherein said heterologous structural gene is a Z-gene coding for β-galactosidase.

32. The bacterial strain of claim 30 wherein said heterologous structural gene is a crystalline insect toxin gene of *Bacillus thuringiensis*.

33. The bacterial strain of claim 30 wherein said heterologous structural gene is a herbicide resistance gene.

34. A method for recognizing a plant cell containing recombinant DNA comprising the steps of:
 (1) transferring into said plant cell recombinant DNA comprising:
  (a) a heat shock promoter which comprises the consensus sequence 5'-C-T-X-G-A-A-X-X-T-A-C-X-X-X-3', where X is A, T, C, or G;
  (b) a transformation recognition gene under the control of said heat shock promoter capable of causing an observable or detectable reaction when expressed;
 (2) applying a stress to said plant cell in which it is desired to recognize those containing recombinant DNA, which stress is capable of inducing a response in said heat shock promoter; and
 (3) observing or detecting the reaction caused by expression of said transformation recognition gene under the control of said heat shock promoter to recognize said plant cell containing recombinant DNA including said transformation recognition gene.

35. The method of claim 34 in which said recombinant DNA comprises at least one additional gene associated with said heat shock promoter and said transformation recognition gene such that the presence of said additional gene may be recognized by the expression of said transformation recognition gene.

36. A method for recognizing a plant cell containing recombinant DNA comprising the steps of:
 (1) transferring into said plant cell recombinant DNA comprising:
  a heat shock promoter which comprises the consensus sequence 5'-C-T-S-G-A-A-M-R-T-A-C-W-M-K-3' where S is C or G; M is A or C; R is A or G; W is A or T; and K is T or G;
  (b) a transformation recognition gene under the control of said heat shock promoter capable of causing an observable or detectable reaction when expressed;
 (2) applying a stress to said plant cell in which it is desired to recognize those containing recombinant DNA, which stress is capable of inducing a response in said heat shock promoter; and
 (3) observing or detecting the reaction caused by expression of said transformation recognition gene under the control of said heat shock promoter to recognize said plant cell containing recombinant DNA including said transformation recognition gene.

37. The method of claim 36 in which said heat shock promoter is derived from soybean.

38. The method of claim 37 wherein said heat shock promoter is selected from the group consisting of hsp2005, hsp2019 and hsp6871.

39. The method of claim 36 wherein said recombinant DNA transferring step comprises
 (a) ligating said heat shock promoter to said transformation recongition gene so that said transformation recognition gene is oriented and positioned with respect to said heat shock promotoer as to be expressed under control thereof, thereby producing recombinant DNA comprising a heat shock inducible transformation recognition gene;
 (b) inserting said heat shock inducible transformation recognition gene into the T-DNA region of a Ti-plasmid of an Agrobacterium strain;
 (c) transferring said recombinant DNA comprising a heat shock inducible transformation recognition gene to said plant cell from said Agrobacterium strain; and
 (d) selecting said plant cell containing said recombinant DNA comprising a heat shock inducible transformation recognition gene for heat shock inducible expression of said transformation recognition gene, thereby demonstrating transformation of said plant cell with said recombinant DNA.

40. The method of claim 39 wherein said Agrobacterium species is *Agrobacterium tumefaciens*.

41. The method of claim 39 wherein said Agrobacterium species is *Agrobacterium rhizogenes*.

42. The method of claim 39 in which said transformation recognition gene is a Z-gene coding for βgalactosidase.

* * * * *

UNITED STATES PATENT AND TRADEMARK OFFICE
CERTIFICATE OF CORRECTION

PATENT NO. : 5,447,858
DATED : Sep. 5, 1995
INVENTOR(S) : Joe L. Key, et al

It is certified that error appears in the above-indentified patent and that said Letters Patent is hereby corrected as shown below:

Column 1: line 64: "(1974) j. Mol." should read --(1974) J. Mol.--; line 68: "7.2:3604" should read --72:3604--.

Column 2: line 8: "Syrup." should read --Symp.--; line 26: "Including" should read --including--; line 56: "β-gal actosidase" should read --β-galactosidase--.

Column 3: line 15: "hornology" should read --homology--; line 19: "oligonucl eotides" should read --oligonucleotides--; line 27: "inducible But" should read --inducible. But--.

Column 4: line 42: "cl ass are" should read --class are--.

Column 5: line 58: "50 pM" should read --50 μM--.

Column 6: line 6: "Blochem." should read --Biochem.--; line 8: "that" should read --those--.

Column 7: line 24: "Kilohess" should read --kilobase--; line 25, "Hind III" should read --HindIII--.

Column 9: line 37: "gene" should read --genes--.

Column 11: line 29: "(Glycine max" should read --(Glycine max--; line 54: "[$^{32}$p]dCP" should read --[$^{32}$p]dCTP--.

UNITED STATES PATENT AND TRADEMARK OFFICE
CERTIFICATE OF CORRECTION

PATENT NO. : 5,447,858
DATED : Sep. 5, 1995
INVENTOR(S) : Joe L. Key, et al

It is certified that error appears in the above-indentified patent and that said Letters Patent is hereby corrected as shown below:

Column 12:
    line 43: "X-DNA" should read --λ-DNA--.

Column 15: lines 49-50: "(5'-TTTCCCGGG" should read --(5'-TTTCCCGGG--;
    line 55: "CCGGG" should read --CCGGG--.

Column 16: line 2: "a Sinai site" should read --a SmaI site--; line 48: "heatshock" should read --heat shock--; line 51: "C cr G." should read --C or G.--.

Column 18: line 54: "recongition" should read --recognition--.

Column 20: lines 4-5: "β galactosidase." should read --β-galactosidase--.

Signed and Sealed this

Twenty-third Day of January, 1996

Attest:

BRUCE LEHMAN

*Attesting Officer*      *Commissioner of Patents and Trademarks*